United States Patent
Numata et al.

(10) Patent No.: US 11,505,577 B2
(45) Date of Patent: Nov. 22, 2022

(54) POLYPEPTIDE COMPRISING CELL-PENETRATING SEQUENCE AND COMPOSITION COMPRISING SAME

(71) Applicant: RIKEN, Saitama (JP)

(72) Inventors: Keiji Numata, Saitama (JP); Kosuke Tsuchiya, Saitama (JP); Yu Miyagi, Saitama (JP); Takaaki Miyamoto, Saitama (JP)

(73) Assignee: RIKEN, Saitama (JP)

( * ) Notice: Subject to any disclaimer, the term of this patent is extended or adjusted under 35 U.S.C. 154(b) by 0 days.

(21) Appl. No.: 16/832,749

(22) Filed: Mar. 27, 2020

(65) Prior Publication Data
US 2020/0347098 A1 Nov. 5, 2020

(30) Foreign Application Priority Data
Mar. 29, 2019 (JP) .............................. JP2019-069134

(51) Int. Cl.
  C07K 14/01 (2006.01)
  C07K 14/00 (2006.01)
(52) U.S. Cl.
  CPC ........ C07K 14/001 (2013.01); *C07K 2319/00* (2013.01)
(58) Field of Classification Search
  CPC .... C07K 14/001; C07K 2319/00; C07K 7/06; C07K 2319/10
  See application file for complete search history.

(56) References Cited

U.S. PATENT DOCUMENTS

2015/0307859 A1  10/2015 Kim
2017/0246266 A1   8/2017 Lee et al.

FOREIGN PATENT DOCUMENTS

| JP | 63030499 A | * | 2/1988 |
| JP | 2016-190813 A | | 11/2016 |
| JP | 2017-527300 A | | 9/2017 |
| JP | 2018-172396 A | | 11/2018 |

OTHER PUBLICATIONS

Tsikaris et al. (International Journal of Biological Macromolecules, 1996, 19(3), 195-205) (Year: 1996).*
Keramisanou et al. (Journal of Peptide Research, 2002, 60(3), 178-185) (Year: 2002).*
Sacco et al (Gazzetta Chimica Italiana, 1997, 127(9), 495-500) (Year: 1997).*
Keller et al (Helvetica Chimica Acta, 1975, 58, 2, 531-541) (Year: 1975).*

Fotin-Mleczek et al., "Endocytosis and Cationic Cell-Penetrating Peptides—A Merger of Concepts and Methods," Curr. Pharm. Des., 2005, 11(28):3613-3628.
Migayi et al., "Cell penetrating peptides (CPPs) containing unnatural a,a-disubstituted amino acid form the stable amphiphilic helical structures and show high cell penetrating ability," 256th ACS National Meeting & Exposition, Aug. 19-23, 2018, Boston, Massachusetts, USA, Program_The American Chemical Society, abstract.
Miyagi et al., "Enhancement of the long-term internalization efficiency of cell penetrating peptide containing a-aminoisobutylic acid having tolerance to protease degradation," Polymer Preprints, Japan, 2018; vol. 67 No. 2, 67th Meeting of the Society of Polymer Science, Japan, Sep. 12 to Sep. 14, 2018, Hokkaido University, Sapporo, Japan, 1U14 with partial English translation.
Miyagi et al., "Synthesis of cell penetrating peptide containing a-aminoisobutylic acid using chemoenzymatic polymerization," Meeting of the Society of Polymer Science, Japan, 2018; 67(1), 67th Meeting of the Society of Polymer Science, Japan, May 23 to May 25, 2018, Nagoya Congress Center, Nagoya, Japan, IG08, with partial English translation.
Miyagi et al., "Synthesis of membrane penetrating peptides containing a-aminoisobutylic acid using chemoenzymatic polymerization," 28th Bio-Polymer Symposium of the Society of Polymer Science, Japan, Jul. 26 to Jul. 27, 2018, Tokyo Institute of Technology, Tokyo, Japan, P21, with partial English translation.
Tsuchiya et al., "Chemoenzymatic Synthesis of Functional Polypeptides," The 6th International Conference on Smart Systems Engineering 2018, Oct. 11-12, 2018, Yamagata University, Yonezawa, Japan, p. 31, IL-4.
Tsuchiya et al., "Development of functional polypeptides for material delivery into plants," The 12th SPSJ International Polymer Conference (IPC 2018), Hiroshima, Japan, Dec. 4-7, 2018.

* cited by examiner

*Primary Examiner* — Sudhakar Katakam
(74) *Attorney, Agent, or Firm* — Foley & Lardner LLP

(57) ABSTRACT

The present application provides: a polypeptide characterized by having an ability of penetrating into a cell and the structure represented by Formula (I)

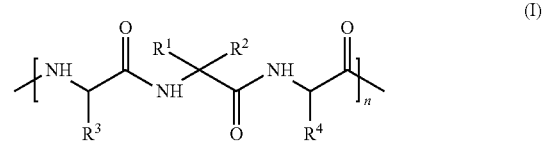

wherein n is a number of 2 to 20; $R^1$ and $R^2$ may independently represent a $C_1$-$C_4$ alkyl group or may bind to each other to form a ring; $R^3$ represents a $C_1$-$C_{10}$ primary aminoalkyl group; $R^4$ represents a hydrogen atom or a $C_1$-$C_{10}$ hydrocarbon group; the "n" number of $R^1$, $R^2$, $R^3$, and $R^4$ may independently be the same with or different from each other; and the N-terminus and the C-terminus may or may not be modified independently; and a cell-invasive composition comprising the polypeptide and a substance of interest.

5 Claims, 10 Drawing Sheets
(4 of 10 Drawing Sheet(s) Filed in Color)
Specification includes a Sequence Listing.

|  | Contents (%)[a] | | | Efficiency ($\times 10^3$)[b] |
| --- | --- | --- | --- | --- |
|  | Helix | Strand | Turn |  |
| P(LysAibGly) | 4 | 36 | 19 | 480 |
| P(LysAibAla) | 26 | 18 | 14 | 280 |
| P(LysAibLys) | 5 | 47 | 21 | 98 |

[a] Calculated by Dichro Web using CONTIN (set 7)
[b] Cellular uptake measured after 16 h incubation L. Whitmore et al, *Nucl. Acids. Res.* 2004, 32, 668-673.
L. Whitmore et al, *Biopolymers*, 2008, 89, 392-400.

Tat (RKKRRQRRR)

P(LysAibAla)

Tat (RKKRRQRRR)

P(LysAibAla)

Tat (RKKRRQRRR)

P(LysAibAla)

```
SEQUENCE LISTING

<160> NUMBER OF SEQ ID NOS: 5

<210> SEQ ID NO 1
<211> LENGTH: 9
<212> TYPE: PRT
<213> ORGANISM: Artificial
<220> FEATURE:
<223> OTHER INFORMATION: peptide

<400> SEQUENCE: 1

Arg Lys Lys Arg Arg Gln Arg Arg Arg
1               5

<210> SEQ ID NO 2
<211> LENGTH: 9
<212> TYPE: PRT
<213> ORGANISM: Artificial
<220> FEATURE:
<223> OTHER INFORMATION: peptide

<400> SEQUENCE: 2

Arg Arg Arg Arg Arg Arg Arg Arg Arg
1               5

<210> SEQ ID NO 3
<211> LENGTH: 28
<212> TYPE: PRT
<213> ORGANISM: Artificial
<220> FEATURE:
<223> OTHER INFORMATION: peptide

<400> SEQUENCE: 3

Lys His Lys His Lys His Lys His Lys His Lys His Lys His Lys His
1               5                   10                  15

Lys His Lys His Lys His Lys His Lys His Lys His
            20                  25

<210> SEQ ID NO 4
<211> LENGTH: 28
<212> TYPE: PRT
<213> ORGANISM: Artificial
<220> FEATURE:
<223> OTHER INFORMATION: peptide

<400> SEQUENCE: 4

Arg His Arg His Arg His Arg His Arg His Arg His Arg His Arg His
1               5                   10                  15

Arg His Arg His Arg His Arg His Arg His Arg His
            20                  25
```

```
<210> SEQ ID NO 5
<211> LENGTH: 10
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (3)..(3)
<223> OTHER INFORMATION: Xaa is Aib.
<220> FEATURE:
<221> NAME/KEY: misc_feature
<222> LOCATION: (6)..(6)
<223> OTHER INFORMATION: Xaa is Aib.
<220> FEATURE:
<221> NAME/KEY: misc_feature
<222> LOCATION: (9)..(9)
<223> OTHER INFORMATION: Xaa is Aib.

<400> SEQUENCE: 5

Cys Lys Xaa Ala Lys Xaa Ala Lys Xaa Ala
1               5                   10
```

POLYPEPTIDE COMPRISING CELL-PENETRATING SEQUENCE AND COMPOSITION COMPRISING SAME

CROSS-REFERENCE TO RELATED APPLICATIONS

This application claims priority to JP 2019-069134, filed Mar. 29, 2019.

The instant application contains a Sequence Listing which has been submitted in ASCII format via EFS-WEB and is hereby incorporated by reference in its entirety. Said ASCII copy, created on Mar. 24, 2020, is named sequence.txt and is 1,659 bytes.

FIELD OF THE INVENTION

The present invention relates to a novel polypeptide comprising a cell-penetrating sequence.

The present invention also relates to a cell-invasive composition comprising the polypeptide and a substance of interest to be introduced into a cell.

The present invention further relates to a method for transporting a substance of interest into a cell using the polypeptide.

BACKGROUND OF THE INVENTION

A cell-penetrating peptide is known as a tool that is extensively used for transporting a substance, such as a certain peptide, protein, or oligonucleotide (also referred to as a "cargo molecule"), into a cell. While such cellular uptake was deduced to occur by directly passing through cell membrane in the beginning, at present, it is known that endocytosis significantly contributes to the cellular uptake (M. Fotin-Mleczek et al, Curr. Pharm. Design., 2005, 11: 3613-3628).

A cell-penetrating peptide is applicable to fields including cellular biology, medicine, and agriculture. For example, a cell-penetrating peptide can be used for intracellular drug delivery, plant variety improvement by genome editing, and cell modification. Although numerous cell-penetrating peptides have been proposed, it is said that desired peptides are (poly)peptides that have properties including the capacity of efficient delivery of a wide variety of cargo molecules into cells without damaging cell membranes. Triggered by the finding in 1988 that the Tat protein, which is an AIDS virus transcription factor, penetrates a cell membrane, the research and development of cell-penetrating peptides, including the Tat peptide, became active.

Examples of cell-penetrating peptides reported include (poly)peptides comprising cationic functional groups including naturally-occurring or non-naturally-occurring amino acids, such as lysine (Lys) or arginine (Arg) (e.g., JP 2016-190813 A), amphipathic (poly)peptides comprising polycationic sequences and polyanionic sequences (e.g., JP 2017-527300 A), and telomerase-derived (poly)peptides (e.g., JP 2018-172396 A).

SUMMARY OF THE INVENTION

While many cell-penetrating peptides have been reported, drawbacks thereof are known. Examples of such peptides include: peptides that disrupt cell membranes to leak the cytoplasm or interrupt normal functions of membrane proteins; peptides that gives rise to a cytotoxic or immunogenic effect; peptides that are rapidly degraded in the cytoplasm; peptides that are captured in the endosome and degraded in that state in the lysosome; peptides that cannot make a cargo molecule free; and peptides that are applicable to a limited range of cargo molecules (Naoki Kajiwara, Futoshi Shibasaki, Journal of the Japanese Pharmacological Society, 2013, 141: 220-221).

Under the above circumstances, there are needs for: cell-penetrating peptides with no or little the above-mentioned drawbacks; or cell-penetrating peptides that are capable of highly efficient cellular uptake of various types of cargo molecules and have low toxicity. In the present invention, we have now found polypeptides having at least properties that they exhibit a higher ability of cell invasion (internalization) over a long period of time compared with conventional cell-penetrating Tat peptide or R9 peptide (polyarginine), that they enable introduction of a cargo molecule into a cell over a long period of time because of high resistance to enzymatic degradation; and that they have almost no cytotoxicity. This has led to the completion of the present invention.

The present invention includes the following features.

[1] A polypeptide represented by Formula (I):

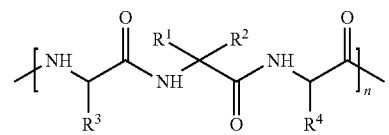

(I)

wherein n is a number of 2 to 20; $R^1$ and $R^2$ may independently represent a $C_1$-$C_4$ alkyl group or may bind to each other to form a ring; $R^3$ represents a $C_1$-$C_{10}$ primary aminoalkyl group; $R^4$ represents a hydrogen atom or a $C_1$-$C_{10}$ hydrocarbon group; the "n" number of $R^1$, $R^2$, $R^3$, and $R^4$ may independently be the same with or different from each other; and the N-terminus and the C-terminus may or may not be modified independently.

[2] The polypeptide according to [1], wherein $R^1$ and $R^2$ are both methyl groups.

[3] The polypeptide according to [1] or [2], wherein $R^4$ is a hydrogen atom or a $C_1$-$C_3$ alkyl group.

[4] The polypeptide according to any of [1] to [3], wherein the C-terminus is modified.

[5] The polypeptide according to any of [I] to [4], wherein the N-terminus is modified.

[6] The polypeptide according to any of [1] to [5], which comprises 2-20 tripeptide units represented by Formula (II):

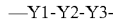

(II)

wherein Y1 is a cationic amino acid selected from the group consisting of Lys and Orn; Y3 is a non-cationic amino acid selected from the group consisting of Gly, Ala, Phe, Leu, Val, and Ile; and Y2 is a non-naturally-occurring amino acid comprising at least one quaternary carbon, each of Y1, Y2, and Y3 is present in a number of 2 to 20 and may independently be the same with or different from each other, and the N-terminus and the C-terminus of the polypeptide may or may not be modified independently.

[7] The polypeptide according to any of [1] to [6], which comprises a reactive functional group on at least one of the N-terminus and the C-terminus.

[8] A cell-invasive composition comprising a polypeptide, as a first polypeptide, according to any of [1] to [7] and a substance of interest, wherein the substance of interest is united with the polypeptide or is present independently from the polypeptide.

[9] The composition according to [8], wherein the substance of interest is selected from the group consisting of a protein, a peptide, a glycoprotein, a naturally-occurring or non-naturally-occurring nucleic acid, DNA, RNA, a DNA/RNA hybrid, an oligonucleotide, a polynucleotide, an anti-sense molecule, miRNA, siRNA, a plasmid, a low-molecular-weight compound, a sugar, a lipid, a glycolipid, a contrast substance, a drug, nanoparticles, and a quantum dot.

[10] The composition according to [8] or [9], wherein one amino acid or a combination of two or more amino acids selected from among Lys, His, and Arg further comprises/comprise a second polypeptide comprising two or more continuous cationic sequences.

[11] The composition according to [10], wherein at least part of the first polypeptide is bound to at least part of the second polypeptide.

[12] A kit for intracellular delivery comprising a polypeptide according to any of [1] to [7].

[13] A method for transporting at least one substance of interest into a cell, comprising bringing a polypeptide according to any of [1] to [7] into contact with a cell and thereby introducing at least one substance of interest into a cell, wherein the substance is united with the polypeptide and/or is present independently from the polypeptide.

According to the present invention, a polypeptide that has almost no cytotoxicity, that has high resistance to enzymatic degradation, and that exhibits a high ability of cell invasion (internalization) over a long period of time, is provided.

BRIEF DESCRIPTION OF THE DRAWINGS

The application file contains at least one drawing executed in color. Copies of this patent application publication with color drawing(s) will be provided by the Office upon request and payment of the necessary fee.

DETAILED DESCRIPTION

Figures 1A, 1B:
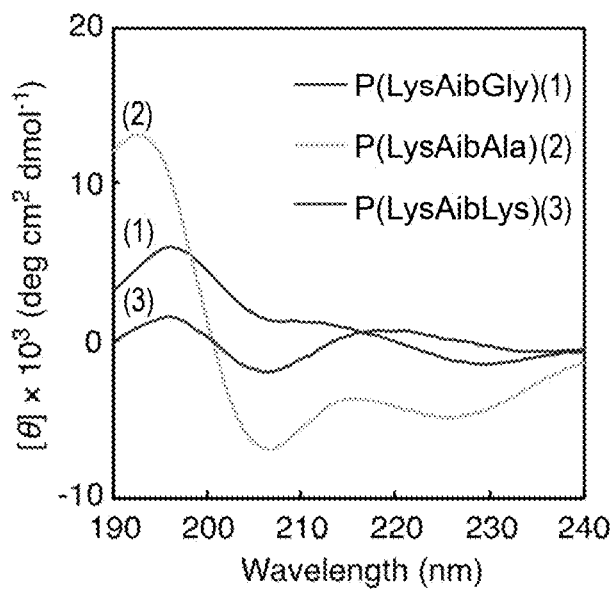
FIG. 1A shows circular dichroism (CD) spectra of the polypeptides of the present invention; i.e., P (LysAibGly), P (LysAibAla), and P (LysAibLys). Herein, "Aib" represents an α-aminoisobutyric acid residue, and "P" represents a multimer (hereinafter, the same meanings are applied)
FIG. 1B shows α helix, β strand, and β turn contents (%) and cellular uptake efficiency (using HEK 293 cells) measured 16 hours after the initiation of incubation.

The present invention will be described in more detail.
1. Polypeptide
The polypeptide of the present invention is represented by Formula (I) below:

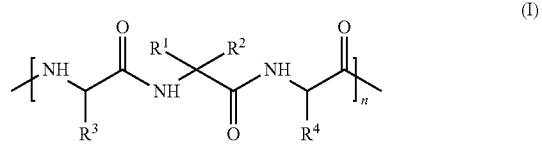

wherein n is a number of 2 to 20; R and R$^2$ may independently represent a C$_1$-C$_4$ alkyl group or may bind to each other to form a ring; R$^3$ represents a C$_1$-C$_{10}$ primary aminoalkyl group; R$^4$ represents a hydrogen atom or a C$_1$-C$_{10}$ hydrocarbon group; the "n" number of R$^1$, R$^2$, R$^3$, and R$^4$ may independently be the same with or different from each other; and the N-terminus and the C-terminus may or may not be modified independently.

In Formula (I), $R^1$ and $R^2$ may independently represent a $C_1$-$C_4$ alkyl group, such as methyl, ethyl, (n- or iso-)propyl, or (n-, sec-, or tert-)butyl group, or $R^1$ and $R^2$ may bind to each other to form a ring. When the ring is formed, it is, for example, a 5-membered or 6-membered cyclic structure. Examples thereof include cyclic or cyclo structures, such as cyclopentyl and cyclohexyl, and heterocyclic structures comprising one of two oxygen atoms, nitrogen atoms, and/or sulfur atoms. Preferably, both of $R^1$ and $R^2$ are methyl groups.

In Formula (I), $R^3$ represents a $C_1$-$C_{10}$ primary aminoalkyl group. Examples of its alkyl group include methyl, ethyl, (n- or iso-)propyl, (n-, sec-, or tert-)butyl, pentyl, isopentyl, neopentyl, hexyl, heptyl, and octyl groups. Preferably, the primary aminoalkyl group is a 4-aminobutyl group.

In Formula (I), $R^4$ represents a hydrogen atom or a $C_1$-$C_{10}$ hydrocarbon group. Examples thereof include alkyl groups, such as methyl, ethyl, (n- or iso-)propyl, (n-, sec-, or tert-)butyl, pentyl, isopentyl, neopentyl, hexyl, heptyl, octyl, nonyl, and decyl groups, and phenyl $C_1$-$C_4$ alkyl groups, such as benzyl and p-hydroxyphenylmethyl groups, and preferably a hydrogen atom or a $C_1$-$C_3$ alkyl group.

The alkyl group and the hydrocarbon group may or may not be substituted independently from each other. When the groups are substituted, the substituent may comprise, for example, at least one group selected from a hydroxyl group, a halogen group, an acyl group, an amino group, a mono- or dialkyl-amino group, an alkoxy group, an alkoxycarbonyl group, a carboxy group, and an alkylthio group.

In Formula (I), the N-terminus and the C-terminus may or may not be modified. When the N-terminus is modified, it may be, for example, acylated with an acyl group (—C═O—R, where R represents a hydrocarbon group such as a $C_1$-$C_{10}$ alkyl group), converted to a urethane group using an alkoxycarbonyl group (—C═O—OR; where R represents a hydrocarbon group such as $C_1$-$C_{10}$ alkyl group), or modified with an alkyl group, such as $C_1$-$C_{10}$ alkyl group in which one or more carbon atoms in the carbon chain may be substituted with a hetero atom such as oxygen, nitrogen, or sulfur. Examples of the acyl groups include $C_1$-$C_{10}$ alkyl groups, such as acetyl, propionyl, butyryl, valeryl, and hexanoyl groups. Examples of the alkoxycarbonyl groups include $C_1$-$C_{10}$ alkoxycarbonyl groups, such as Boc. Examples of the alkyl group are $C_1$-$C_{10}$ alkyl groups, and examples of the alkyl groups include polyethylene glycol and oligoethylene glycol residues.

The C-terminus is modified via, for example, esterification or amidation. In the case of esterification, the hydroxyl (OH) group of the C-terminal carboxy group may be substituted with, for example, a $C_1$-$C_{10}$ alkoxy group. In the case of amidation, the hydroxyl (OH) group of the C-terminal carboxy group may be substituted with, for example, a $C_1$-$C_{10}$ monoalkylamino or dialkylamino group or an amino group.

When at least one of the N-terminus and the C-terminus has a reactive functional group, the functional group can bind to a substance of interest described below or another polypeptide used in combination to form a complex. The reactive functional group is not particularly limited. When an addition reaction between a maleimide group and a thiol group is employed, for example, the terminus may be modified with a maleimide-containing modification group, a thiol-containing modification group (cysteine), or the like.

Specifically, the polypeptide of the present invention comprises 2-20 tripeptide units represented by Formula (II):

$$—Y1-Y2-Y3— \quad (II)$$

wherein Y1 is a cationic amino acid selected from the group consisting of Lys and Orn; Y3 is a non-cationic amino acid selected from the group consisting of Gly, Ala, Phe, Leu, Val, and Ile; and Y2 is a non-naturally-occurring amino acid comprising at least one quaternary carbon, each of 2 to 20 Y, Y2, and Y3 may independently be the same with or different from each other, and the N-terminus and the C-terminus of the polypeptide may or may not be modified independently from each other.

Symbols indicating amino acids used herein are as follows: Lys (or K) represents lysine, Orn represents ornithine, Gly (or G) represents glycine, Ala (or A) represents alanine, Phe (or F) represents phenylalanine, Leu (or L) represents leucine, Val (or V) represents valine, Ile (or I) represents isoleucine, Arg (or R) represents arginine, His (or H) represents histidine, Gln (or Q) represents glutamine, and Cys (or C) represents cysteine.

In Formula (II), Y2 is a non-naturally-occurring amino acid comprising at least one quaternary carbon. Examples thereof include, but are not limited to, α-ethylalanine, α-butylalanine, α-propargylalanine, α,α-diethylglycine, and 1-aminocyclepentane carboxylic acid. Preferably, Y2 is α-aminoisobutyric acid (Aib). As used herein, the "quaternary carbon (atom)" means a carbon atom having 4 adjacent carbon atoms bound thereto.

More specifically, the polypeptides of the present invention is represented by Formula (II), wherein Y1 is Lys, Y2 is Aib, and Y3 is a non-cationic amino acid selected from the group consisting of Gly, Ala, Phe, Leu, Val, and Ile.

The amino acids of Y and Y3 may optionally be substituted with D-amino acids, respectively, whereby the stability against a hydrolase, such as protease or peptidase, can be more improved.

The polypeptide of the present invention may be in the form of a salt, where needed. Preferable salts include pharmaceutically acceptable acid addition salts. Examples thereof include acid addition salts formed with inorganic acids (e.g., hydrochloric acid, phosphoric acid, and sulfuric acid) and acid addition salts formed with organic acids (e.g., acetic acid, propionic acid, fumaric acid, maleic acid, succinic acid, tartaric acid, citric acid, malic acid, oxalic acid, benzoic acid, and methansulfonic acid). Alternatively, examples thereof include acid addition salts formed with inorganic bases (e.g., alkali metals such as sodium and potassium and alkaline earth metals such as calcium and magnesium) and acid addition salts formed with organic bases (e.g., trimethylamine, triethylamine, pyridine, picoline, ethanolamine, diethanolamine, and triethanolamine).

2. Synthesis of Polypeptide

The polypeptide of the present invention may be synthesized by, for example, a method comprising the following steps.

<Step 1>

In this step, a tripeptide represented by Formula (II) is prepared.

A tripeptide is prepared by a conventional peptide synthesis method (e.g., the Merrifield's method (Merrifield, Recent Progress in Hormone Res., 23: 451, 1967)). This method comprises successively binding α-amino acids with protected side chain to insoluble resin carrier (i.e., a solid phase). Specifically, the carboxy group of a first α-amino acid with protected side chain is bound to a linker bound to the solid phase, followed by deprotection of the α-amino group, and a second α-amino acid with protected side chain, in which the carboxy group is modified with an active group, is bound (coupled) thereto, followed by deprotection of the second α-amino acid, and then a third α-amino acid with protected side chain is coupled, followed by deprotection of the third α-amino acid and cleavage of the linker, and finally the synthesized tripeptide is recovered and purified.

The tripeptide of interest may be isolated and purified by performing, for example, solvent extraction, chromatography (e.g., gel filtration, ion-exchange chromatography, affinity chromatography, or reverse phase chromatography), high-performance liquid chromatography, and recrystallization, appropriately in combination.

<Step 2)>

This step includes procedures as described below. The C-terminal carboxy group of the tripeptide synthesized in Step 1 is esterified (e.g., methyl- or ethyl-esterified) and, where needed, the ε-amino group of lysine (Lys) is protected. Subsequently, the tripeptide (e.g., about 0.05 mM to about 0.5 mM) is subjected to enzyme-catalyzed polymerization reaction in a buffer (e.g., pH 7-8), such as phosphate buffer or citrate buffer, in the presence of a protease (e.g., about 1 mg/ml to about 200 mg/ml), such as papain, proteinase K, trypsin, cathepsin B, plasmin, bromelain, or chymotrypsin, at about 40° C. to about 60° C. for about 10 minutes to about 4 hours. After centrifugation, the purified precipitate is recovered and then thoroughly washed with pure water to obtain a white solid. Where the ε-amino group of lysine (Lys) is protected, then additional step of removing the protective group from the final product may be performed. For example, when the protective group is Boc group, it can be removed under acidic conditions, such as trifluoroacetic acid or HCl-ethyl acetate.

With the use of the enzyme-catalyzed polymerization reaction that we have developed (e.g., Yu Miyagi et al., Symposium on Macromolecules, Vol. 66, No. 2, 1C06, 2017; K. Tsuchiya, K. Numata, Chem. Commun., 2017, 53: 7318-7321), multimers of the tripeptide polymer (e.g., dimer to 20-mer) can be readily synthesized. The synthetic method is not limited to the above-mentioned methods and may also include the production using the Fmoc solid-phase method.

3. Cell-Invasive Composition

The present invention also provides a cell-invasive composition comprising the polypeptide described in section 1 above and a substance of interest, wherein the substance is united with the polypeptide or is present independently from the polypeptide.

As used herein, the "cell-invasive" refers to a property that the substance of interest is capable of penetrating a cell membrane and invading into a cell. Such cell invasion occurs via endocytosis. Endocytosis is the mechanism that a substance, such as an extracellular molecule, (i.e., "a substance of interest" as used herein) is incorporated into a cell through the clathrin-coated vesicle (Junko Toshima, Jiro Toshima, Biochemistry, 2014, 86 (6): 788-792). The polypeptide comprising a cell-penetrating sequence described in section 1 above is capable of forming a complex with a substance of interest and transporting the substance into a cell.

The term "substance of interest" as used herein refers to a substance that is intended to transport (or deliver) it into a cell. The substance is also referred to as a "cargo molecule."

Such substance may be a naturally-occurring product or a non-naturally-occurring substance that is also referred to as an "artificial product" or "synthetic product". Examples of the substance include, but are not limited to, proteins, peptides, glycoproteins, naturally-occurring or non-naturally-occurring nucleic acids, DNA, RNA, DNA/RNA hybrids, oligonucleotides, polynucleotides, anti-sense molecules, miRNA, siRNA, plasmids, low-molecular-weight compounds, sugars, lipids, glycolipids, contrast substances, drugs, nanoparticles, and quantum dots. The term "drug" as used herein is a broad concept including substances for treatment, alleviation, prevention, and diagnosis of diseases or pathological symptoms.

According to one embodiment, the substance of interest contained in the composition may be united with the polypeptide to form a complex.

The term "complex" as used herein refers to, for example, the form in which a substance of interest is covalently or noncovalently bound (or conjugated) to the polypeptide or the form in which a substance of interest is included in or attached to at least one polypeptide molecule. In the latter form, one or two or more polypeptides of the present invention may be used for the inclusion of a substance of interest. Alternatively, one or more polypeptides of the present invention may be used in combination with one or more other substances (e.g., other polypeptides, polymers, organic compounds, or inorganic compounds). In such a case, one or more polypeptides of the present invention may be covalently or noncovalently bound to one or more other substances.

Examples of noncovalent bonds include hydrogen bond, electrostatic interaction (or ionic bond), the van der Waals force, and hydrophobic bond. As the polypeptide of the present invention comprises a cationic portion and a non-cationic portion (e.g., hydrophobic portion), nucleic acids, such as polynucleotides, having phosphodiester bonds are capable of binding to the polypeptide due to the electrostatic interaction.

In the case of covalent bonds, a substance of interest can directly or indirectly (for example, via a linker) bind to the C-terminus or the N-terminus of the polypeptide of the present invention. In each case, the terminal amino or carboxy group may comprise an active group that is easy to bind to a functional group of the substance of interest, or may comprise an active group that is easy to bind to the C-terminus or the N-terminus of the polypeptide at a site that does not adversely affect the physiological activity of the substance of interest. In general, the amino group is known to bind to compounds, such as isothiocyanate, isocyanate, acyl azide, N-hydroxysuccinimide ester, sulfonyl chloride, aldehyde, glyoxal, epoxide, oxirane, carbonate, aryl halide, imide ester, carbodiimide, anhydride, and fluoroester. Thus, such reactive group may be introduced into the polypeptide or the substance of interest.

The linker is any chemical group that does not adversely affect the physiological activity of a substance of interest, and examples of the linker include polyoxyalkylene, where the alkylene is, for example, $C_2$-$C_{10}$ alkylene. Specifically, the linker is a sarcosine linker represented by the formula below:

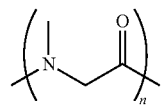

wherein "n" is a number of 2-20, for example 3-12, 4-8, or 5-7.

Moreover, when the substance of interest is inclosed in or attached to a plurality of polypeptide molecules, the substance of interest may be partially or completely inclosed in the space of a structure formed by the plurality of polypeptide molecules by, for example, the van der Waals force, hydrophobic bond, or physical effect.

The composition of the present invention may comprise additives such as carriers, preservatives, solubilizes, pH modifies, or (fluorescent) probes, in addition to the polypeptide and the substance of interest.

The composition of the present invention may be in the form of, for example, solid or liquid.

According to another embodiment, the substance of interest may be present independently from (or separately from) the polypeptide in the composition. As used herein, the term "present independently from" refers to the state that no interaction is observed between the substance of interest and the polypeptide based on analytical data, and thus said term should be construed as a term having the broadest sense including any other embodiments than the "united with" the polypeptide. For example, when the composition is in a solid form, the substance of interest and the polypeptide are dissolved in a carrier such as aqueous medium (e.g., physiological saline, buffer, buffered saline, or water) before the substance of interest contacts with the cells that the substance penetrates, thereby forming the complex in situ.

The ratio of the polypeptide and the substance of interest (mol/mol) is unlimitedly, for example, 0.1-5, preferably 0.5-2.

Furthermore, according to one embodiment, the composition of the present invention further comprises a second polypeptide in which a combination of one or more basic amino acids selected from among Lys (K), His (H), and Arg (R) comprises 2 or more (e.g., 2-50, 2-40, 2-30, 3-30, or 5-30) continuous cationic sequences. According to another embodiment, the substance of interest (e.g., DNA) and the second polypeptide undergo ionic interaction to form a complex. In such complex, the substance of interest may be surrounded by the second polypeptide so that the substance is included in the polypeptide. In the composition according to this embodiment, at least a part of the first polypeptide may be covalently bound to at least a part of the second polypeptide (e.g., by covalently binding via a linker). That is, at least a part of the second polypeptide including the substance of interest may be modified with the first polypeptide. Also, as mentioned above, the first polypeptide may be covalently bound to the second polypeptide via a linker. Although the linker is not particularly limited, an example of the linker is a linker comprising a group formed by the addition reaction of a maleimide group and a thiol group.

4. Kit for Intracellular Delivery

The present invention further provides a kit for intracellular delivery comprising the polypeptide described in section 1 above.

The kit can comprise the substance of interest described in section 3 above, in addition to the polypeptide.

The kit may further comprise, for example, a carrier (or diluent) such as an aqueous medium or a (fluorescent) probe.

The kit may further comprise instructions for intracellular delivery. The instructions may include procedures for bringing the polypeptide of the present invention into contact with the substance of interest in a diluent, precautions, and the like.

5. Method for Transporting Substance into Cell

The present invention further provides a method for transporting a substance into a cell comprising bringing the polypeptide described in section 1 above into contact with a cell to introduce at least one substance of interest, which is united with the polypeptide and/or is present independently from the polypeptide, into the cell.

According to the method of the present invention, pathways or mechanisms by which the substance of interest is transported into the cell are not limited. The transport pathways or mechanisms vary depending on, for example, molecular structures, properties, and the ratio of the polypeptide, the substance of interest, or other substances used in combination in some embodiment of the present invention, the state of substances, and the strength of interactions between substances. In the embodiment that the polypeptide is present independently from the substance of interest, the substance tends to be transported via macropinocytosis, which is a type of endocytosis, although the transport pathway is not limited thereto.

The polypeptide and the target cell are as described in sections 1 and 2 above. In the methods described above, the composition and/or the kit of the present invention comprising the polypeptide may be used.

The cells are eucaryotic cells, including, for example, animal cells, plant cells, yeast cells, filamentous cells, and basidiomycetous cells.

Preferable animal cells are, for example, insect cells and vertebrate cells, and preferable vertebrate cells are, for example, mammalian cells and avian cells. Preferable mammalian cells include, for example, human cells, canine cells, feline cells, rodent cells, and ungulate cells. Examples of rodent animals include mice, rats, hamsters, and rabbits. Examples of ungulate animals include bovines, horses, pigs, and camels.

Examples of plant cells include any cells of angiosperms, such as dicotyledonous and monocotyledonous plant cells, and any cells of gymnosperms, bryophytes, herbaceous, pteridophyte plants, and woody plants. Specific examples of plants include plants of: Solanaceae, such as *Solanum melongena* L., *Solanum lycopersicum, Capsicum annuum* L. var. angulosum Mill., *Capsicum annuum* L., and *Nicotiana tabacum* L.; Gramineae, such as *Oryza sativa, Triticum aestivum* L., *Hordeum vulgare* L., *Lolium perenne* L., *Lolium multiflorum* Lam., *Festuca pratensis* Huds., *Festuca arundinacea* Schreb., *Dactylis glomerata* L., and *Phleum pratense* L.; Brassicaceae, such as *Arabidopsis thaliana, Brassica campestris* L., *Brassica oleracea* L. var. *capitata* L., *Raphanus sativus* L., and *Brassica campestris* L., *B. napus* L.; Leguminosae, such as *Glycine max, Vigna angularis* Willd., *Phaseolus vulgaris* L., and *Vicia faba* L.; Cucurbitaceae, such as *Cucumis sativus* L., *Cucumis melo* L., *Citrullus* vulgaris Schrad., *C. moschata* Duch., and *C. maxima* Duch.; Convolvulaceae, such as *Ipomoea batatas;* Liliaceae, such as *Allium fistulosum* L., *Allium cepa* L., *Allium tuberosum* Rottl., *Allium sativum* L., and *Asparagus officinalis* L.; Labiatae, such as *Perilla frutescens* Britt. var. *crispa*; Compositae, such as *Chrysanthemum morifolium, Chrysanthemum coronarium* L., *Lactuca sativa* L. var. *capitata* L., and *Brassica pekinensis* Rupr.; Rosaceae, such as Rose *hybrida* Hort. and *Fragaria×ananassa* Duch.; Rutaceae, such as *Citras unshiu* and *Zanthoxylum piperitum* DC.; Myrtaceae, such as *Eucalyptus globulus* Labill; Salicaceae, such as *Populas nigra* L. var. *italica* Koehne; Chenopodiaceae, such as *Spinacia oleracea* L. and *Beta vulgaris* L.; Gentianaceae, such as *Gentiana scabra* Bunge var. buergeri Maxim.; and Caryophyllaceae, such as *Dianthus caryophyllus* L.

Examples of the cells include, but are not limited to, cells in the body of an organism, cells removed from an organism, primary cultured cells, established cells, deposited cells, germ cells (e.g., oocytes, gonocytes, plant egg cells, and plant sperm cells), stem cells (e.g., somatic stem cells, embryonic stem (ES) cells, and induced pluripotent stem (iPS) cells), and diseased cells.

An example of the substance of interest is a substance capable of affecting properties, such as functions, traits, and molphorogies of cells, when introduced into the cell.

In the method of the present invention, the polypeptide is brought into contact with cells.

According to the method of the present invention, properties and conditions of the target cell with which the polypeptide is contacted are not particularly limited. Even cells having cell wall, such as plant cells and yeast cells, can be used as target cells without pretreatment for cell wall removal. The cell wall may be destroyed by treatment with enzymes, such as lysozymes, to prepare protoplasts or spheroplasts, which may be used as target cells. The target cells with which the polypeptide is contacted may be organized or unorganized. According to an embodiment in which plant cell is a target cell, specifically, the polypeptide may be contacted with, for example, a plant individual, plant tissue, such as seeds, leaves, stems, or roots that may or may not be treated, or callus (an undifferentiated plant cell mass).

An example is as described below.

When the polypeptide is contacted with the cells, the cells may be cultured in an adequate medium, to which cells a given amount of the polypeptide and the substance of interest may be added, and incubated at an adequate temperature for an adequate period of time. Where the polypeptide is labeled with a fluorescent substance (e.g., FITC), cellular invasion by the polypeptide can be observed under, for example, fluorescent microscopes.

When the polypeptide is contacted with a plant tissue, such as leave or root, the polypeptide may be controlled to come into contact with a given site of the tissue using an instrument such as syringe or dropper.

The substance of interest transported (or, introduced or delivered) into the cell may be used such that the substance can play a function as intended in the cell. Examples of such use include, but are not limited to, the following.

When the substance of interest is used for gene therapy, a vector such as plasmid, which comprises a correct gene to substitute for a disease gene, can be used as the substance of interest to transport it into cells of an affected tissue or organ.

When the substance of interest is used for treatment of tumor, an anti-tumor agent can be used as the substance of interest to transport it into cells of tumor tissue. In such a case, a complex prepared in a nano-size comprising the polypeptide and the antitumor agent is easy to be delivered to the tumor tissue through the capillary blood vessel.

When the substance of interest is used for genome editing, for example, the Crispr-Cas9 complex can be used as the substance of interest to transport it into the target cell. According to the method, for example, the substance of interest can be used for improvement of plant varieties.

When the substance of interest is used for modification of cells, for example, a transcription factor for modification of a somatic cell into an iPS cell can be delivered into the cell.

The composition of the present invention may be administered to an organism (e.g., a mammal including a human) orally or parenterally (e.g., by means of an injection, ocular instillation, nasal drip, transpulmonary administration, percutaneous administration, or intraventricular administration), preferably injection (e.g., intravenous administration). The administration may be, for example, systemic administration via intravenous administration or topical administration by injection directly into a lesion.

EXAMPLES

The present invention will be described more specifically with reference to the following examples, although the scope of the present invention is not limited to these examples.

Example 1

<Materials>

In the examples below, materials obtained from Watanabe Chemical Industries, Ltd., Tokyo Chemical Industry Co., Ltd., FUJIFILM Wako Pure Chemical Corporation, or Sigma-Aldrich, were used.

Tripeptide esters used as monomers in the chemical enzyme-catalyzed polymerization reaction were synthesized in the manner described below.

Papain obtained from FUJIFILM Wako Pure Chemical Corporation was used. The activity thereof is approximately $0.5\ Ug^{-1}$. A unit is defined as the amount of papain required for hydrolysis of 1 mole of N-benzoyl-dl-arginine-p-nitroanilide per minute at pH 7.5 and 25° C.

Proteinase K derived from *Tritirachium album* obtained from FUJIFILM Wako Pure Chemical Corporation was used. The activity was 21 U/mg. One unit is defined as the amount of proteinase K that generates a peptide equivalent to 1 μmol of tyrosine by the reaction using hemoglobin as a substrate and the Folin-Ciocalteu reagent as a coloring substance in phosphate buffer (pH 7.5) at 37° C. for 1 minute.

The Dulbecco's Modified Eagle Medium (DMEM) was obtained from FUJIFILM Wako Pure Chemical Corporation and used as a cell culture medium.

The human embryonic kidney (HEK) cells (ATCC, Cat. No. CRL-1573) were cultured in a DMEM medium supplemented with fetal bovine serum (FBS), non-essential amino acids (0.1 mM), L-glutamine (2 mM), and 1 v/v % penicillin-streptomycin in a 5% $CO_2$ incubator at 37° C.

Protein concentration was identified using the XL-Bradford assay kit (Aproscience Inc.).

A cytolytic buffer was obtained from Promega Corporation (U.S.A.).

For visualization of confocal microscopic observation, cells were stained with the DNA-binding dye Hoechst 33342 obtained from Thermo Fisher Scientific (U.S.A.).

<Measurement>

$^1H$ (500 MHz) and $^{13}C$ (125 MHz) NMR spectra were obtained using the Varian NMR spectrometer.

IR spectra were obtained using the IRPrestige-21 spectrometer (Shimadzu Corporation).

Matrix-assisted laser desorption/ionization-time of flight (MALDI-TOF) mass spectrometry was carried out using the ultrafleXtreme MALDI-TOF spectrometer (Bruker Daltonics (U.S.A.)) at the acceleration voltage of 15 kV in a reflective mode. The sample was dissolved in water/acetonitrile (0.8 mg/ml) containing 0.1% trifluoroacetic acid (TFA), mixed with a solution of α-cyano-4-hydroxycinnamic acid (CHCA) in water/acetonitrile (10 mg/ml), and then deposited on a target plate (MTP 384 ground steel BC target plate).

CD spectra were obtained using the spectropolarimeter (J-820, JASCO).

Fluorescent spectra were obtained using the spectrometer (FP-8500, JASCO).

Analysis by reverse-phase high-performance liquid chromatography (RP-HPLC) was performed using the HPLC system having the auto-sampler AS-2055, the gradient pump PU2089, the column oven CO-4060, the UV/vis detector UV-4075, and the quaternary gradient pump PU-2089 Plus (JASCO), and the YMC-Triart C18 column (particle size: 5 μm, 150×3 mm, YMC) at 25° C. and a flow rate of 1 ml/min.

The mobile phase was composed of acetonitrile (Effluent A), Milli-Q water (Effluent B), and Milli-Q water supplemented with 0.1 v/v % TFA (Effluent C). Boc-Gly was used as the internal standard. In order to analyze proteolytic stability of the polypeptide, 100 μl of the polypeptide sample solution supplemented with Boc-Gly was injected into the column, and the composition of the mobile phase was linearly changed from Effluent A:B:C of 88%:2%:10% to Effluent A:B:C of 64%:26%:10% over a period of about 24 minutes for elution.

<Synthesis of Monomer>

In the synthesis examples below, "Boc" represents a tert-butoxycarbonyl group. When "Boc" is added to an arbitrary amino acid, it is represented that the amino group of such amino acid is protected by Boc (tert-butoxycarbonyl group). "Z" represents a benzyloxycarbonyl group. When "Z" is added to any amino acid, it is represented that the amino group of such amino acid is protected by Z. When "OEt" is added to any amino acid, it is represented that the carboxylic acid of such amino acid is converted into Et (ethyl)ester.

"Aib" represents an α-aminoisobutyric acid, "Gly" represents glycine, "Lys" represents lysine, "Ala" represents alanine, "Phe" represents phenylalanine, and "Leu" represents leucine.

<Synthesis of HCl.AibGly-OEt>

Boc-Aib (4.06 g, 20.0 mmol), HCl.Gly-OEt (2.79 g, 20 mmol), and 1-hydroxybenzotriazole.monohydrate (HOBt.H$_2$O) (2.97 g, 22.0 mmol) were mixed with stirring using a stirrer bar in a flask, and the mixture was dissolved in chloroform (CHCl$_3$) at 0° C. in the nitrogen atmosphere. After triethylamine (2.79 ml, 20.0 mmol) was added, a solution of 1-ethyl-3-(3-dimethylaminopropyl)carbodiimide hydrochloride (EDC-HCl) (4.22 g, 22.0 mmol) in chloroform was added dropwise over a period of about 30 minutes. The solution was stirred at 0° C. for 1 hour and then at 25° C. for 24 hours. The solution was washed with an aqueous solution of 5% Na$_2$CO$_3$. The organic layer was dried over MgSO$_4$. After MgSO$_4$ was separated by filtration, the organic solvent was concentrated using a rotary evaporator to obtain a white solid. The white solid was dissolved in dichloromethane at 0° C. TFA (11.5 ml, 150 mmol) was then added to the solution, and the mixture was stirred at 25° C. The organic solvent was removed under a reduced pressure 24 hours later. A sticky solid was obtained in quantitative yield.

<Synthesis of Lys(Boc)AibGly-OEt>

Z-Lys (Boc) (3.80 g, 10 mmol), HCl.AibGly-OEt (2.25 g, 10.0 mmol), and HOBt.H$_2$O (1.49 g, 11.0 mmol) were mixed with stirring using a stirrer bar in a flask, and the mixture was dissolved in 10 ml of chloroform (CHCl$_3$) at 0° C. in the nitrogen atmosphere. After triethylamine (1.39 ml, 10.0 mmol) was added, a solution of EDC.HCl (2.11 g, 11.0 mmol) in chloroform was added dropwise thereto over a period of approximately 30 minutes. The solution was stirred at 0° C. for 1 hour and then at 25° C. for 24 hours. The solution was washed with an aqueous solution of 5% Na$_2$CO$_3$. The organic layer was dried over MgSO$_4$. After MgSO$_4$ was separated by filtration, the organic solvent was concentrated using a rotary evaporator. With the use of hexane and ethyl acetate as an effluent, the crude product was purified via silica gel chromatography. Z-Lys(Boc)AibGly-OEt was obtained as a white solid. Z-Lys(Boc)AibGly-OEt was dissolved in methanol (47.5 ml). After bubbling nitrogen gas in the solution for 15 minutes, palladium supported on carbon (0.525 g, 10 wt %) was added with caution. After the nitrogen atmosphere was replaced with the hydrogen atmosphere, the solution was stirred at 25° C. for 48 hours. The solution was filtered through celite, and the filtrate was concentrated under a reduced pressure.

The resulting sticky solid was dispersed in water and then lyophilized. Lys(Boc)AibGly-OEt was obtained as a white solid. The yield was 69°%.

$^1$H NMR (500 MHz, CDCl$_3$): δ1.16 (t, 3H, —OCH$_2$CH), 1.22 (m, 2H, —CH* (CH$_2$CH$_2$—)—), 1.30-1.47 (m, 13H, —C(CH$_3$), —C(CH$_3$)$_2$—, —CH* (CH$_2$CH$_2$CH$_2$—)—), 1.66 (m, 2H, —CH* (CH$_2$—)—), 2.88 (m, 2H, —CH$_2$NHCOC(CH$_3$)$_3$), 3.63 (m, 1H, —CH* (CH$_2$—)—), 3.78 (m, 2H. —COCH$_2$NH—), 4.05 (m, 2H, —OCH$_2$CH$_3$), 6.77 (m, 1H, —CH$_2$NHCOC(CH$_3$)), 8.22 (t, 1H, —C(CH$_2$)$_2$NHCO—), 8.41 (m, 2H, —NH$_2$), 8.82 (m, 1H, —CH$_2$NHCO—)

$^{13}$C NMR (132 MHz, CDCl$_3$): δ14.1, 21.6, 23.5, 26.5, 28.3, 30.0, 30.4, 40.9, 52.3, 56.3, 60.3, 77.4, 155.6, 168.0, 169.8, 173.9

IR (neat): 3296, 3217, 3047, 2980, 2939, 2873, 1168, 1529, 1456, 1392, 1366, 1252, 1173, 1018, 935, 864, 781 cm$^{-1}$.

<Synthesis of HCl.AibAla-OEt>

HCl.AibAla-OEt was synthesized in the same manner as in the case of HCl.AibGly-OEt except for the use of Boc-Aib and HCl.Ala-OEt as starting materials. HCl.AibAla-OEt was obtained as a white sticky solid in quantitative yield.

<Synthesis of Lys(Boc)AibAla-OEt>

Lys(Boc)AibAla-OEt was synthesized in the same manner as in the case of Lys(Boc)AibGly-OEt except for the use of HCl.AibGly-OEt as a starting material. Lys(Boc)AibAla-OEt was obtained as a white sticky solid. The yield was 84%.

$^1$H NMR (500 MHz, CDCl$_3$): δ1.16 (t, 3H, —OCH$_2$CH$_3$), 1.27 (m, 2H, —CH* (CH$_2$CH$_2$—)—), 1.30-1.45 (m, 18H, —C(CH$_3$)$_3$, —CH* (CH$_3$)—, —C(CH$_3$)$_2$—, —CH* (CH$_2$CH$_2$CH$_2$—)—), 1.67 (m, 2H, —CH* (CH$_2$—)—), 2.87 (m, 2H, —CH$_2$NHCOC(CH$_3$)$_3$), 3.56 (m, 1H, —CH* (CH$_2$—)—), 3.81 (m, 1H, —COCH(CH$_3$)NH—), 4.04 (m, 2H, —OCH$_2$CH), 4.23 (m, 1H, —CH* (CH$_3$)—), 6.74 (m, 1H, —CH$_2$NHCOC(CH$_3$)), 7.92 (t, 1H, —C(CH$_2$)$_2$NHCO—), 8.36 (m, 2H, —NH$_2$), 8.78 (m, 1H, —CH$_2$NHCO—)

$^{13}$C NMR (132 MHz, CDCl$_3$): δ14.0, 16.8, 21.6, 23.5, 26.2, 28.3, 30.0, 47.9, 52.3, 56.2, 60.3, 66.4, 77.4, 155.6, 168.0, 172.6, 173.2

IR (neat): 3381, 3244, 2982, 2940, 2874, 1688, 1520, 1454, 1391, 1366, 1271, 1250, 1215, 1175, 1053, 1020, 866 cm$^{-1}$.

<Synthesis of HCl.AibLeu-OEt>

HCl.AibLeu-OEt was synthesized in the same manner as in the case of HCl.AibGly-OEt except for the use of Boc-Aib and HCl.Leu-OEt as starting materials. HCl.AibLeu-OEt was obtained as a white sticky solid in quantitative yield.

<Synthesis of Lys(Boc)AibLeu-OEt>

Lys(Boc)AibLeu-OEt was synthesized in the same manner as in the case of Lys(Boc)AibGly-OEt except for the use of HCl.AibLeu-OEt as a starting material. Lys(Boc)AibLeu-OEt was obtained as a white sticky solid. The yield was 51%.

$^1$H NMR (500 MHz, CDCl$_3$): δ0.85 (m, 6H, —CH(CH$_3$)$_2$), 1.15 (t, 3H, —OCH$_2$CH$_3$), 1.20-1.45 (m, 20H, —CH* (CH$_2$CH$_2$—)—, —C(CH$_3$)$_3$, —CH* (CH$_3$)—, —C(CH$_3$)$_2$—, —CH* (CH$_2$CH$_2$CH$_2$—)—), 1.51 (m, 1H, —CH(CH$_3$)$_2$), 1.67-1.79 (m, 2H, —CH* (CH$_2$CH(CH$_3$)$_2$)—, —CH* (CH$_2$—)—), 2.86 (m, 2H, —CH$_2$NHCOC(CH$_3$)$_3$), 3.37 (m, 1H, —CH* (CH$_2$—)—), 3.82 (m, 1H, —COCH(CH$_2$—)NH—), 4.06 (m, 2H, —OCH$_2$CH$_3$), 4.27 (m, 1H, —CH* (CH$_3$)—), 6.74 (m, 1H, —CH$_2$NHCOC(CH$_3$)), 7.92 (t, 1H, —C(CH$_2$)$_2$NHCO—), 8.36 (m, 2H, —NH$_2$), 8.78 (m, 1H, —CH$_2$NHCO—)

$^{13}$C NMR (125 MHz, CDCl$_3$): δ14.1, 21.0, 21.3, 23.0, 23.9, 26.2, 28.3, 30.3, 50.5, 50.8, 52.3, 56.3, 60.3, 60.6, 77.3, 155.5, 168.0, 172.0, 173.3

IR (neat): 3331, 3208, 3046, 2959, 2870, 1682, 1516, 1456, 1386, 1366, 1271, 1252, 1173, 1030, 945, 864, 777 cm$^{-1}$.

<Synthesis of HCl.AibLys(Boc)-OMe>

Z-Aib (6.17 g, 26.0 mmol), HCl.Lys (Boc)-OMe (7.71 g, 26.0 mmol), and HOBt-H$_2$O (3.86 g, 28.6 mmol) were mixed using a stirrer bar in a flask, and the mixture was dissolved in 25 ml of CHCl$_3$ at 0° C. in the nitrogen atmosphere. After triethylamine was added, a solution of EDC-HCl (5.48 g, 28.6 mmol) was added dropwise thereto over a period of approximately 30 minutes. The solution was stirred at 0° C. for 1 hour and then at 25° C. for 24 hours. The solution was washed with an aqueous solution of 5% Na$_2$CO$_3$. The organic layer was dried over MgSO$_4$. After MgSO$_4$ was separated by filtration, the organic solvent was concentrated using a rotary evaporator. The resulting sticky solid was dissolved in 130 ml of methanol. After bubbling nitrogen gas in the solution for 15 minutes, palladium supported on carbon (1.25 g, 10 wt %) was added with caution. After the nitrogen atmosphere was replaced with the hydrogen atmosphere, the solution was stirred at 25° C. for 48 hours. The solution was filtered through celite, and the filtrate was concentrated under a reduced pressure. HCl.AibLys(Boc)-OMe was obtained as a white sticky solid in quantitative yield.

<Synthesis of Lys(Boc)AibLys(Boc)-OMe>

Z-Lys(Boc) (9.21 g, 24.2 mmol), HCl.AibLys(Boc)-OMe (8.35 g, 24.2 mmol), and HOBt-H$_2$O (3.60 g, 26.6 mmol) were mixed using a stirrer bar in a flask, and the mixture was dissolved in 25 ml of CHCl$_3$ at 0° C. in the nitrogen atmosphere. The solution was stirred at 0° C. for 1 hour and then at 25° C. for 24 hours. The solution was washed with an aqueous solution of 5% Na$_2$CO$_3$. The organic layer was dried over MgSO$_4$. After MgSO$_4$ was separated by filtration, the organic solvent was concentrated using a rotary evaporator. With the use of hexane and ethyl acetate as an effluent, the crude product was purified via silica gel chromatography. Z-Lys(Boc)AibLys(Boc)-OEt was obtained as a white solid. The white solid was dissolved in 60 ml of MeOH. After bubbling nitrogen gas in the solution for 15 minutes, palladium supported on carbon (0.864 g, 10 wt %) was added with caution. After the nitrogen atmosphere was replaced with the hydrogen atmosphere, the solution was stirred at 25° C. for 48 hours. The solution was filtered through celite, and the filtrate was concentrated under a reduced pressure. The resulting sticky solid was dispersed in water and then lyophilized. Lys(Boc)AibLys(Boc)-OMe was obtained as a white solid. The yield was 63%.

$^1$H NMR (500 MHz, CDCl$_3$): δ1.15-1.45 (m, 32H, —CH* (CH$_2$CH$_2$—)—×2, —C(CH$_3$)$_3$×2, —C(CH$_3$)$_2$—, —CH* (CH$_2$CH$_2$CH$_2$—)—×2), 1.70-1.85 (m, 4H, —CH* (CH$_2$—)—×2), 2.76 (m, 2H, —CH$_2$NHCOC(CH$_3$)$_3$), 2.87 (m 2H. —CH$_2$NHCOC(CH$_3$)$_3$), 3.60 (m, 3H, —OCH$_3$), 3.86 (m, 1H, —CH* (CH$_2$—)—), 4.20 (m, 1H, —CH* (CH$_2$—)—), 6.76 (m, 2H, —CH$_2$NHCOC(CH$_3$)×2), 7.79-7.87 (m, 1H, —NHCO—), 7.65-8.50 (m, 1H, —NHCO—), 8.78-8.86 (m, 2H, —NH$_2$)

$^{13}$C NMR (125 MHz, CDCl$_3$): δ26.3, 28.3, 29.0, 38.2, 56.3, 77.3, 155.5, 168.0, 172.7, 173.4

IR (neat): 3331, 2976, 2934, 2866, 1682, 1514, 1445, 1391, 1366, 1271, 1250, 1171, 1040, 1007, 866, 781 cm$^{-1}$.

<Synthesis of HCl.AibPhe-OEt>

HCl.AibPhe-OEt was synthesized in the same manner as in the case of HC-AibGly-OEt except for the use of Boc-Aib and HCl.Phe-OEt as starting materials. HCl.AibPhe-OEt was obtained as a white sticky solid in quantitative yield.

<Synthesis of Lys(Boc)AibPhe-OEt>

Lys(Boc)AibPhe-OEt was synthesized in the same manner as in the case of Lys(Boc)AibGly-OEt except for the use of HCl.AibPhe-OEt as a starting material. Lys(Boc)AibPhe-OEt was obtained as a white sticky solid. The yield was 63%.

$^1$H NMR (500 MHz, CDCl$_3$): δ1.06 (t, 3H, —OCH$_2$CH$_3$), 1.20-1.45 (m 16H, —CH* (CH$_2$CH$_2$—)—, —C(CH$_3$)$_3$, —C(CH$_3$)$_2$—, —CH* (CH$_2$CH$_2$CH$_2$—)—), 1.67 (m, 2H, —CH* (CH$_2$—)—), 2.88 (m, 2H, —CH* (CH$_2$Ar)—), 3.03 (m, 2H, —CH$_2$NHCOC(CH$_3$)$_3$), 3.80 (m, 1H, —CH* (CH$_2$—)—)3.99 (m, 2H, —OCH$_2$CH$_3$), 4.39 (m, 1H, —CH* (CH$_2$Ar)—), 6.79 (m, 1H, —CH$_2$NHCOC(CH$_3$)), 7.15-7.35 (m, 5H, Ar), 7.94 (m, 1H, —NHCO—), 8.26 (m, 1H, —NHCO—), 8.61 (m, 2H, —NH$_2$)

$^{13}$C NMR (125 MHz, CDCl$_1$): δ13.9, 21.6, 24.0, 25.6, 28.3, 30.6, 36.7, 52.3, 54.1, 56.3, 60.4, 77.4, 126.4, 128.2, 129.2, 137.6, 155.6, 168.1, 171.4, 173.3

IR (neat): 3379, 3285, 3059, 2980, 2938, 2870, 1724, 1688, 1651, 1518, 1443, 1389, 1366, 1350, 1275, 1217, 1171, 1140, 1030, 995, 864, 743, 700 cm$^{-1}$ <Polymerization of Tripeptide Esters>

Each polymerization was carried out in a glass tube. The polymerization was basically carried out as described below. A solution of papain or proteinase K (50 mg/ml) was added to a solution of each tripeptide ester ([M]$_0$=0.1-0.2 mM) in phosphate buffer (1 M, pH 8.0), the resulting solution was stirred at 40° C. or 60° C. for 10-60 minutes, and then the precipitate was recovered by centrifugation (9,000 rpm, 15 min) and washed 2 times with Milli-Q water. The resultant was lyophilized to obtain each polypeptide as white powder at a yield of 9-54%.

Table 1 shows the polypeptides obtained.

TABLE 1

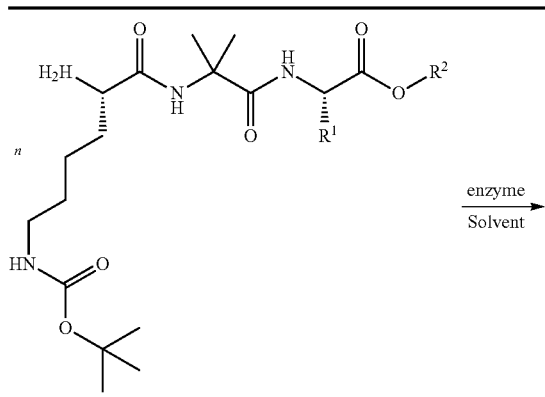

TABLE 1-continued

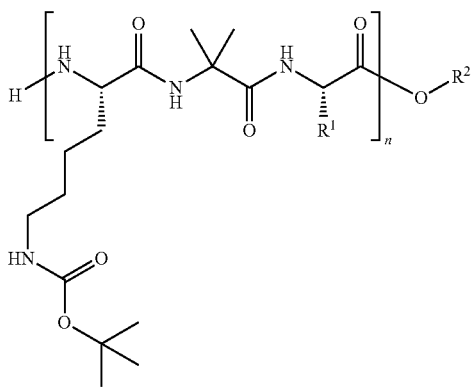

| monomer [a] | [M]₀ (mM) | enzyme | [E]₀ (mg/ml) | solvent [b] | temp (° C.) | time (min) | yields (%) | $DP_{max}$ [c] |
|---|---|---|---|---|---|---|---|---|
| LysAibGly | 0.1 | papain | 50 | PB | 40 | 10 | 8.8 | 7 |
| LysAibAla | 0.1 | papain | 50 | PB | 60 | 60 | 11.4 | 4 |
| LysAibLeu | 0.2 | papain | 50 | CB | 60 | 60 | 9.2 | 3 |
| LysAibLys | 0.1 | papain | 30 | PB | 60 | 60 | 26.5 | 3 |
| LysAibPhe | 0.1 | ProK | 2.5 | PB | 60 | 60 | 54.0 | 3 |

[a]: The monomer sequences of the tripeptides obtained (Lys-Aib-Xxx, where Xxx is Gly, Ala, Leu, Lys, or Phe). The side-chain functional group of Lys is protected by Boc. In the formula, $R^1$ represents H, $CH_3$, $CH_2(CH_3)_2$, $CH_2Ph$, or $(CH_2)_4$-Boc; and $R^2$ represents $CH_3$ or $CH_2CH_3$.
[b]: PB represents a phosphate buffer (1.0 M, pH 8.0); and CB represents a citrate buffer (1.0 M, pH 7.0).
[c]: DPmax was deduced from MALDI-TOF MS signals.

<Deprotection of Boc Group>

Each polypeptide was dissolved in TFA in a flask at 25° C. The solvent was removed under a reduced pressure 24 hours later. The product was lyophilized to obtain a deprotected polypeptide as white powder. The yield was 11-55%.

<Synthesis of Tetramethylrhodamine (TAMRA)-Labeled Polypeptide>

Each peptide was labeled with tetramethylrhodamine (TAMRA) in the manner described below.

A solution of tetramethylrhodamine-5-isothiocyanate in dimethyl sulfoxide (DMSO) was added to the peptide solution. The resulting solution was stirred at 25° C. for 14 hours. The mixture was poured into excess Milli-Q water. The precipitate was collected by centrifugation and washed with Milli-Q water. The resultant was lyophilized to obtain a pink solid at a yield of 11-55%.

<Evaluation>
<Circular Dichroism (CD) Spectroscopy>

CD spectra were obtained using the JASCO J-820 spectropolarimeter. The measurement was carried out using a quartz cuvette (optical path length, 0.1 cm). Spectra were collected in a rage of from 190 nm to 240 nm. The 30 μM solution of each peptide (P (LysAibXaa): Xaa=Gly, Ala, Leu, Lys, and Phe) supplemented with 0.1 wt % sodium dodecyl sulfate (SDS) was assayed at 20° C. in the nitrogen atmosphere. The data are indicated as the mean residual mass ellipticity (deg cm² dmol⁻¹). The concentration of each peptide solution was adjusted based on the concentration of repeating units of each peptide.

The results are shown in FIG. 1A and FIG. 1B.

The results of the measurement of CD spectra indicated that P (LysAibGly) represented by Formula (I) of the present invention forms a random secondary structure and that P (LysAibAla) forms a secondary structure comprising many helix structures compared with P (LysAibLys) outside the scope of the present invention.

<Heparin Assay>

Affinity between each TAMRA-labeled peptide and heparin sulfurate was evaluated using spectropolarimetry. For the assay, the polypeptide and the heparin sulfurate in 4 mM sodium phosphate buffer (pH 7.2) containing NaCl (150 mM) were prepared. The peptide solution was mixed with the heparin sulfurate solution. The final concentration of the peptide was adjusted to 50 nM as determined based on the absorbance at 543 nm ($\Delta\epsilon$=88,000 cm⁻¹ M⁻¹). After the mixture was incubated at 25° C. for 30 minutes, the fluorescent anisotropy at 570 nm was measured by fluorescent spectroscopy using a polarizer (excited at 490 nm). For normalization of the data, the fluorescent anisotropy in the absence of heparin sulfurate was designated to be the standard.

Figure 2:
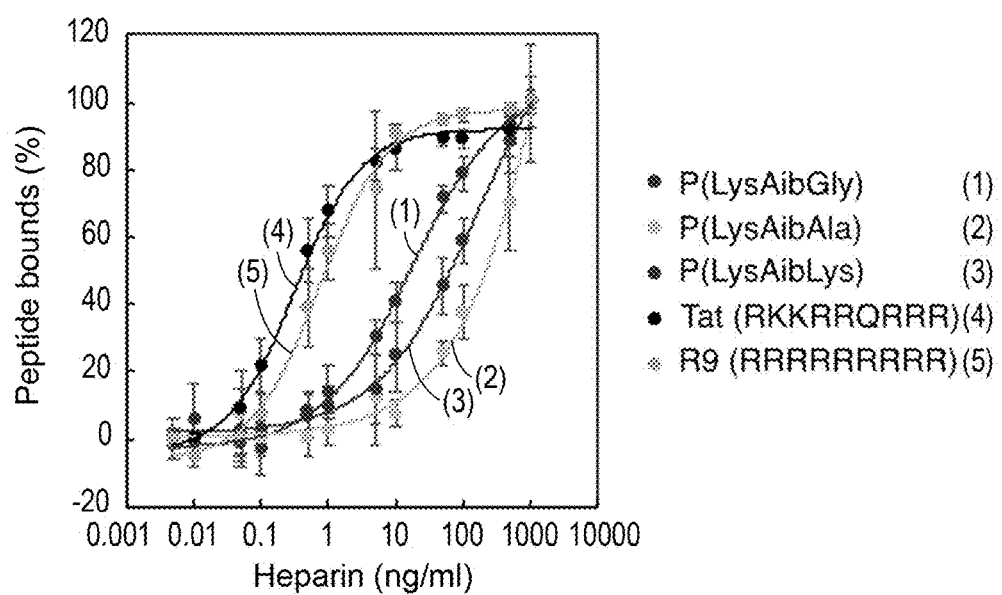
FIG. 2 shows binding affinity of each of the following (poly)peptides with heparin sulfuric acid as measured by fluorescence polarization in a phosphate buffer containing 150 mM NaCl (pH 7.4), the (poly)peptides being: the TAMRA-labeled polypeptides of the present invention, i.e. P (LysAibGly), P (LysAibAla), and P (LysAibLys), and comparative peptides, i.e. Tat peptide (RKKRRQRRR (SEQ ID NO: 1)) and R9 peptide (RRRRRRRRR (SEQ ID NO: 2)).

The results are shown in FIG. 2. As comparable examples, the results of heparin assays of Tat (RKKRRQRRR (SEQ ID NO: 1)) and R9 (RRRRRRRRR (SEQ ID NO: 2)) synthesized by the solid-phase peptide synthesis are also shown.

From the results of the heparin assays, P (LysAibGly) and P (LysAibAla) represented by Formula (I) of the present invention are considered to have cell-membrane adsorption properties lower than those of the known cell-penetrating sequences Tat and R9. The assay results demonstrated that P (LysAibGly) and P (LysAibAla) are substances that can be efficiently introduced into cells without remaining on the cell membrane.

<Proteolytic Stability Assay>

Ten (10) mM phosphate buffer (pH 7.2) containing each polypeptide (1 mg/ml) and 10 mM phosphate buffer (pH 7.2) containing trypsin (10 μg/ml) were incubated at 37° C. and then stirred at 1,000 rpm to mix them. Several hours later, 60 μl of the peptide solution was poured into 150 μl of 1% TFA to inactivate trypsin. After 30 μl of the Boc-Gly solution was added as the internal standard, the mixture was centrifuged at 13,500 rpm to precipitate the inactivated trypsin. The supernatant was subjected to RP-HPLC analysis, and the peak area was calculated to determine the amount of the residual polypeptide.

Figure 3:
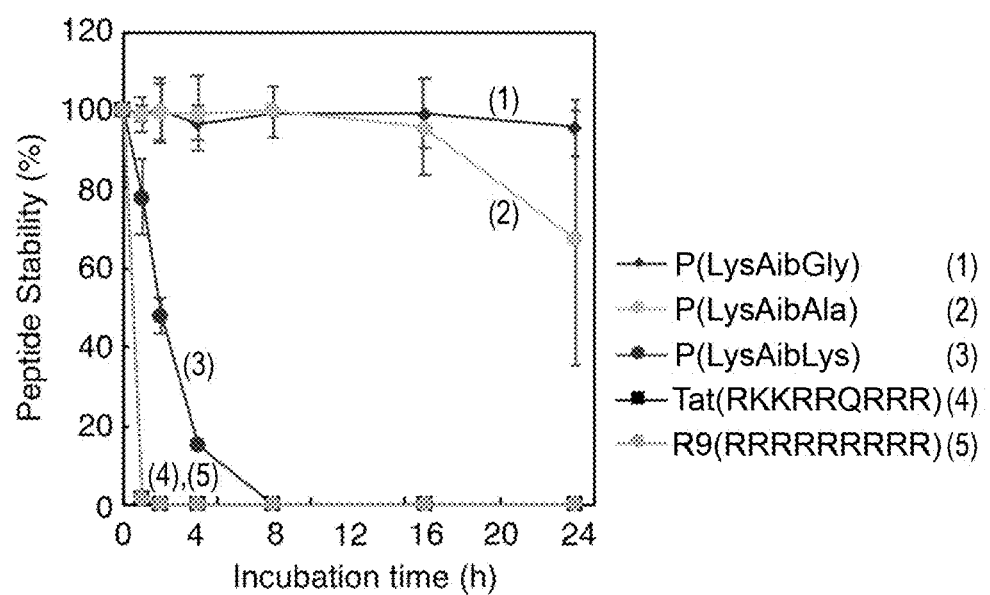
FIG. 3 shows the assay results of stability against proteolysis by trypsin of: the polypeptides of the present invention, i.e. P (LysAibGly), P (LysAibAla), and P (LysAibLys); and comparative peptides, i.e. Tat peptide and R9 peptide.

The results are shown in FIG. 3. As comparative examples, the results of Tat and R9 are also shown.

The results of the proteolytic stability assay demonstrated that P (LysAibGly) and P (LysAibAla) represented by Formula (I) of the present invention have the registance to enzymatic degradation higher than that of P (LysAibLys) outside the scope of the present invention and than those of the known cell-penetrating sequences Tat and R9, because P (LysAibGly) and P (LysAibAla) each comprise the non-naturally-occurring amino acid residue Aib in their sequences. That is, P (LysAibGly) and P (LysAibAla) remain stable for a long period of time inside and outside the cells.

<Evaluation of Each Polypeptide for Cell-Penetrating Properties into Animal Cells>

HEK 293 cells were seeded on a 24-well culture plate (20,000 cells/well) and incubated in 1 ml DMEM containing FBS at 37° C. in the presence of 5% $CO_2$. The medium was exchanged with 500 µl of a fresh medium containing 10% FBS and 5 µM each polypeptide sample 24 hours later. After the incubation, the medium was removed, and the cells were subjected to trypsin treatment in 400 µl of trypsin-EDTA for 15 minutes. The detached cells were centrifuged at 4° C. and at 1,600 rpm for 3 minutes and then collected. The cell pellet was dispersed in PBS, and the dispersion was centrifuged at 4° C. and at 1,600 rpm for 3 minutes. The resultant was treated with a cytolytic buffer, and the cell pellet was homogenized using a homogenizer. The cell debris was removed by centrifugation at 13,500 rpm, and the supernatant was subjected to respective assays. Using a microplate reader, the fluorescent intensity of each lysate was measured at 570 nm. In order to normalize the relative fluorescent unit (RFU) depending on the protein weight, the Bradford protein assay kit was used to determine a protein level in each well.

Figure 4:
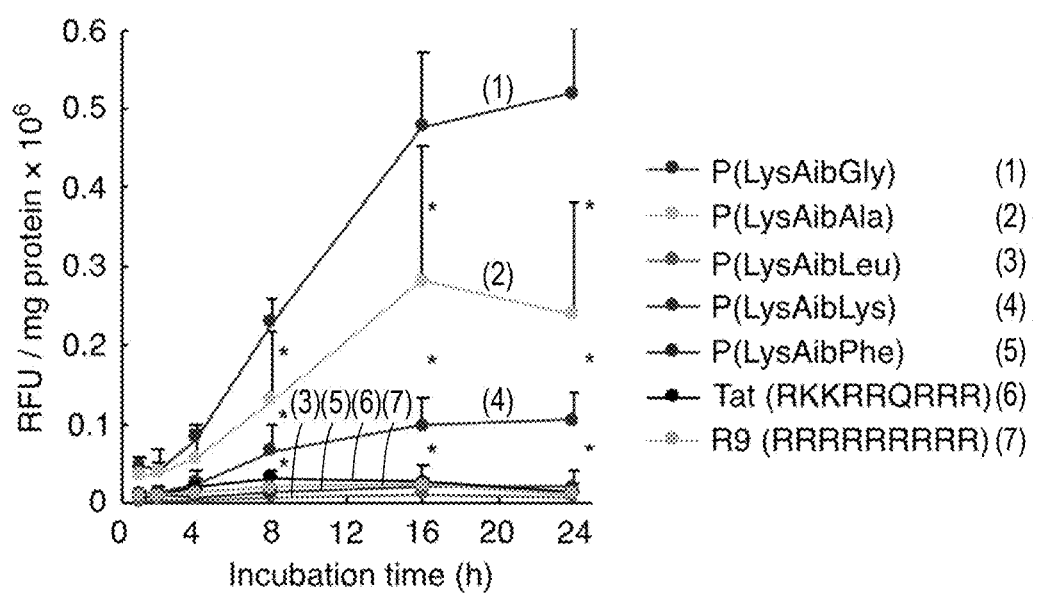
FIG. 4 shows intracellular uptake (represented by relative fluorescence unit (RFU)/mg protein×10⁶) of: the polypeptides of the present invention, i.e. P (LysAibGly), P (LysAibAla), and P (LysAibLys), and comparative peptides, i.e. Tat peptide and R9 peptide, in HEK 293 cells.

The results are shown in FIG. 4. As comparative examples, the results of Tat and $R^9$ are also shown.

The results demonstrated that P (LysAibGly) and P (LysAibAla) represented by Formula (I) of the present invention exhibited a higher ability of cell invasion (internalization) over a long period of time compared with the conventional cell-penetrating sequences Tat and R9. That is, P (LysAibGly) and P (LysAibAla) serve as cell-penetrating peptides that are capable of introducing into cells over a long period of time because of high resistance to enzyme degradation.

<Cell Viability>

HEK 293 cells were seeded on a 96-well culture plate (2,500 cells/well) in 100 g of DMEM containing FBS. The plate was incubated at 37° C. in the presence of 5% $CO_2$. The medium was exchanged with 100 µl of a fresh medium containing each 5 µM polypeptide sample 24 hours later. After the incubation, the medium was removed, and the cells were washed twice with 100 µl of a fresh medium. In the end, each well was filled with 100 µl of a fresh medium, and 20 µl of the CellTiter 96 $AQ_{ueous}$ One Solution Reagent® (Promega Corporation) was added to each well. After incubation was carried out at 37° C. in the presence of 5% $CO_2$ for 2 hours, the absorption of each well was measured at 490 nm using a 96-well plate reader.

Figure 5:
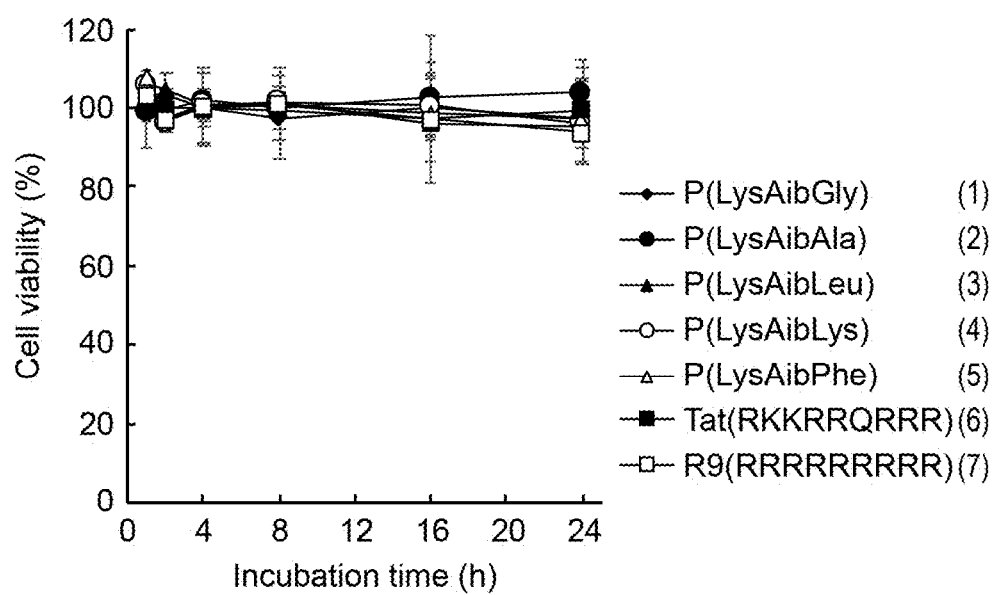
FIG. 5 shows HEK 293 cell viability (%) in the presence of: the polypeptides of the present invention, i.e. P (LysAibGly), P (LysAibAla), and P (LysAibLys); and comparative peptides, i.e. Tat peptide and R9 peptide, at a range of concentrations exhibiting the ability of cell penetration.
Figure 6A:
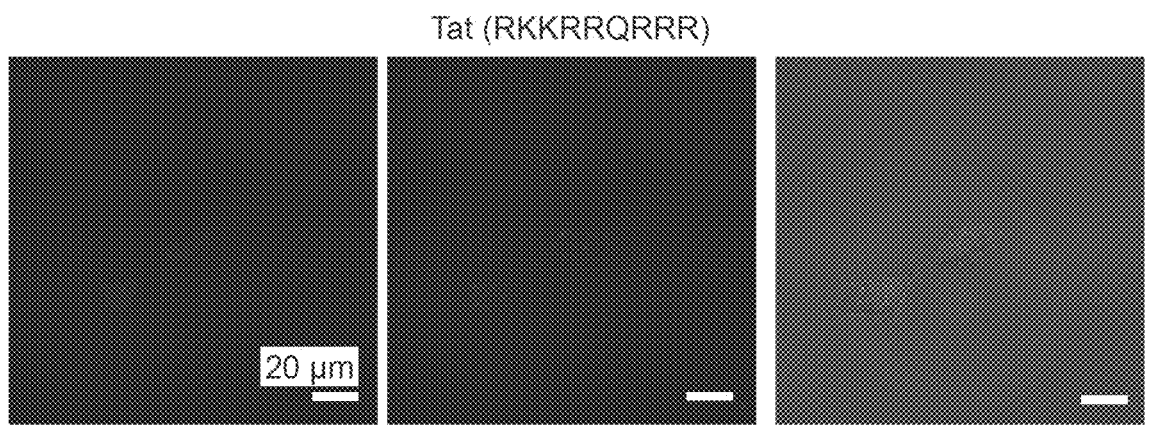
FIGS. 6A and 6B show images of survived HEK 293 cells treated with Tat peptide and P (LysAibAla), respectively, obtained under confocal laser scanning microscopic observation. The left panels show the images of the cells counterstained with the nuclear marker Hoechst 33342. The center panels show the images of the cells incubated with the 5 μM peptide (labeled with TAMRA) indicated, in the presence of 5% CO$_2$ at 37° C. for 2 hours. The right panels show the images of the merged cells.
Figure 6B:
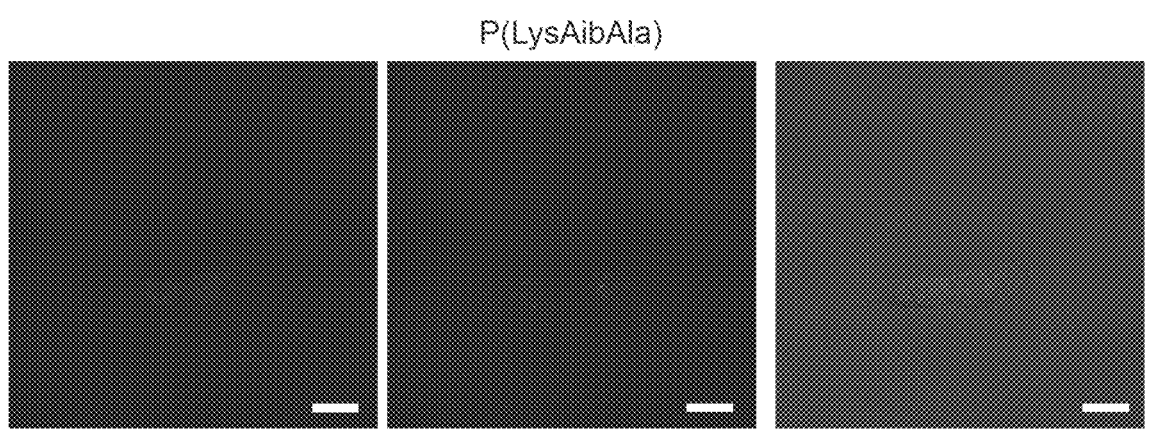
Figure 7A:
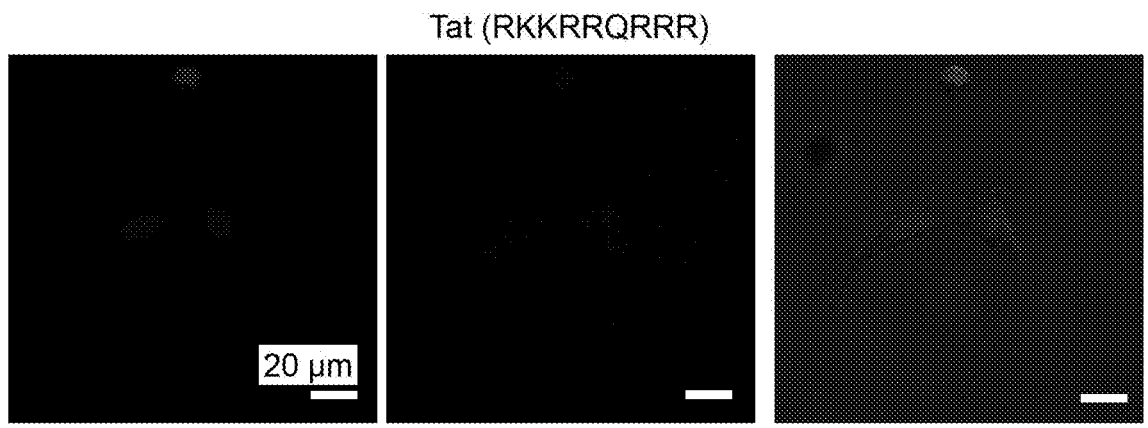
FIGS. 7A and 7B show images of survived HEK 293 cells treated with Tat peptide and P (LysAibAla), respectively, obtained under confocal laser scanning microscopic observation. The left panels show the images of the cells counterstained with the nuclear marker Hoechst 33342. The center panels show the images of the cells incubated with the 5 μM peptide (labeled with TAMRA) indicated, in the presence of 5% CO$_2$ at 37° C. for 8 hours. The right panels show the images of the merged cells.
Figure 7B:
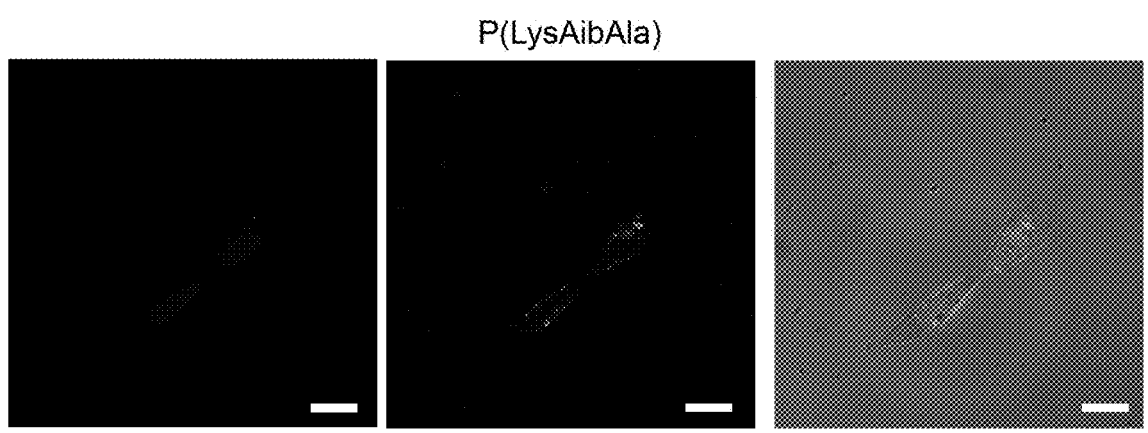
Figure 8A:
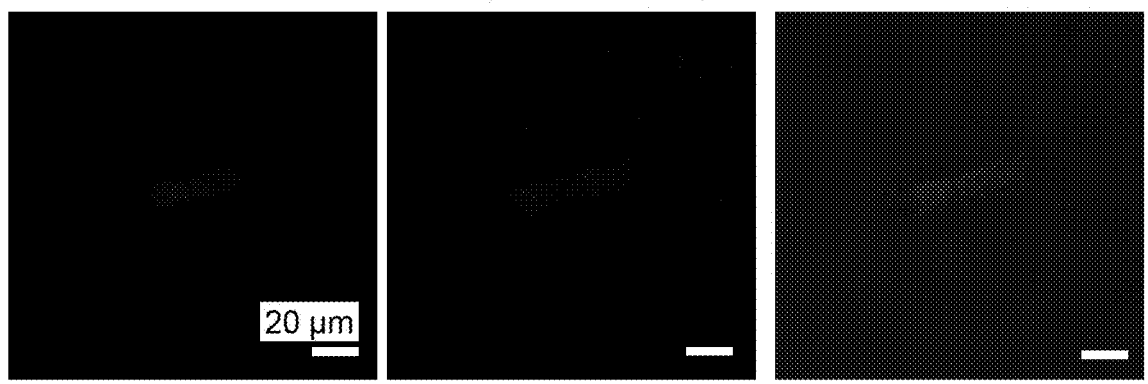
FIGS. 8A and 8B show images of survived HEK 293 cells treated with Tat peptide and P (LysAibAla), respectively, obtained under confocal laser scanning microscopic observation. The left panels show the images of the cells counterstained with the nuclear marker Hoechst 33342. The center panels show the images of the cells incubated with the 5 μM peptide (labeled with TAMRA) indicated, in the presence of 5% CO$_2$ at 37° C. for 16 hours. The right panels show the images of the merged cells.
Figure 8B:
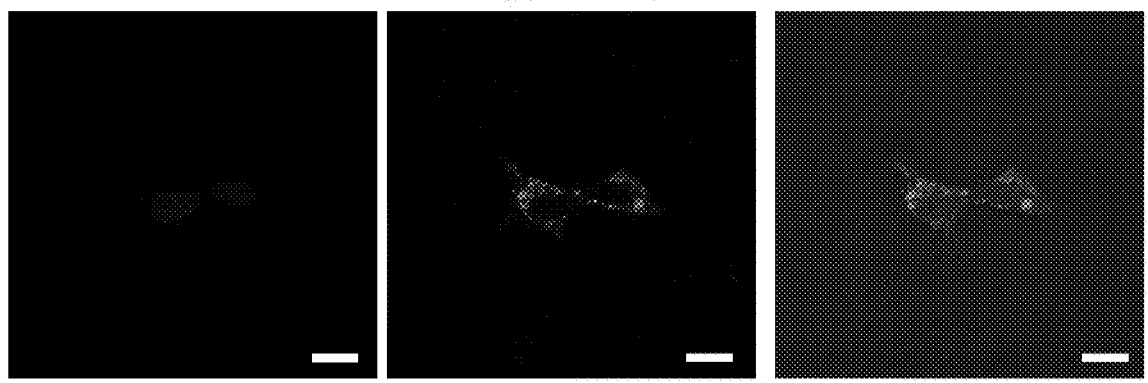

The results are shown in FIG. 5.

FIG. 5 demonstrates that P (LysAibGly) and P (LysAibAla) represented by Formula (I) of the present invention exert no cytotoxicity within a range in which P (LysAibGly) and P (LysAibAla) exhibit an ability of cell invasion (internalization) as with the conventional cell-penetrating sequences Tat and R9.

<Evaluation of Polypeptide Internalization into Animal Cells Using Confocal Laser Scanning Microscope (CLSM)>

HEK 293 cells in 1 ml of DMEM containing FBS were seeded on a 3.5-cm dish. After incubation was carried out for 24 hours, the medium was exchanged with 500 µl of a fresh medium containing FBS and each polypeptide sample. The final concentration of the polypeptide was 5 µM. After incubation was carried out for 2, 8, and 16 hours, the medium was removed from each well, and the cells were incubated with 500 µl of fresh DMEM containing Hoechst 33342 at 37° C. for 15 minutes. The medium was removed, and the dish was filled with fresh DMEM. The fluorescent signals of the Hoechst 33342 nuclear marker and each tetramethylrhodamine-labeled polypeptide were observed at the excitation wavelengths of 405 nm and 555 nm (diode), respectively, using the confocal laser scanning microscope LSM700 (Carl Zeiss, Oberkochen, Germany). The co-localization analysis of microscopic images was carried out using the operating software Zen2011.

The results are shown in FIGS. 6A, 6B, FIGS. 7A, 7B, and FIGS. 8A, 8B.

FIGS. 6A, 6B, FIGS. 7A, 7B, and FIGS. 8A, 8B demonstrated that P (LysAibAla) represented by Formula (I) of the present invention was more efficiently introduced into the cell over a long period of time, compared with the conventional cell-penetrating sequence Tat.

<Evaluation of Each Polypeptide for Cell-Penetrating Properties into Plant Cells and for Internalization into Plant Cells>

Leaves from *Alabidopsis thaliana* (YFPox) expressing the yellow fluorescent protein (YFP) in the cytoplasm were cut into circles each having a diameter of 1 cm. The leaf sections were placed in a 1.5-ml tube and soaked in 100 µl of each TAMRA-labeled polypeptide (50 µM) at 0.08 MPa for 1 minute and at −0.08 MPa for 1 minute. The treated leaf sections were incubated in the dark at 25° C. for 3 hours. Using CSLM, the leaf sections were subjected to quantitative evaluation for polypeptide internalization. Intracellular distribution of the TAMRA-labeled polypeptide was directly observed at the excitation wavelength of 555 nm (diode).

Figure 9A:
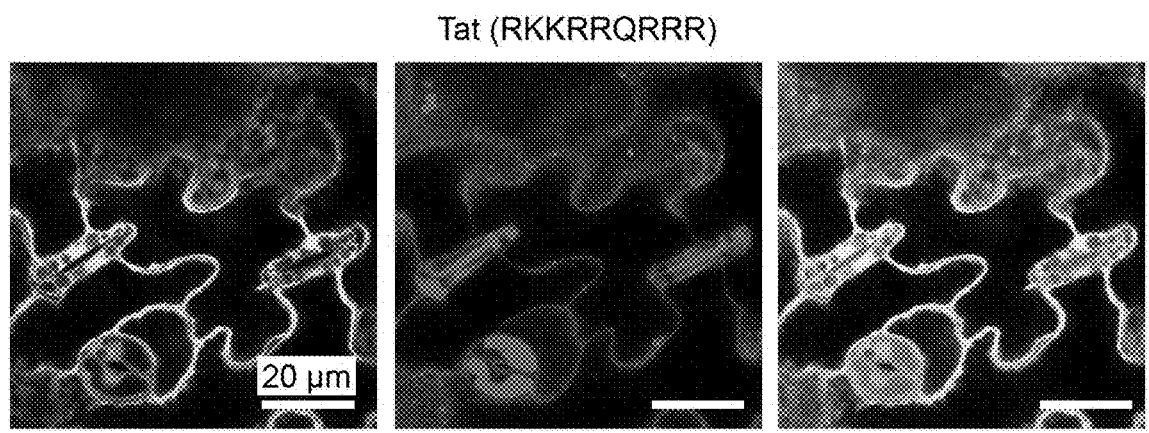
FIGS. 9A and 9B show images of *Arabidopsis* leaf epidermis treated with Tat peptide and P (LysAibAla), respectively, obtained under confocal laser scanning microscopic observation. The left panels show the images of the leaf epidermis having YFP (yellow fluorescent protein). The center panels show the images of the cells incubated at 25° C. for 3 hours with the 50 μM peptide (labeled with TAMRA) indicated. The right panels show the images of the merged cells.
Figure 9B:
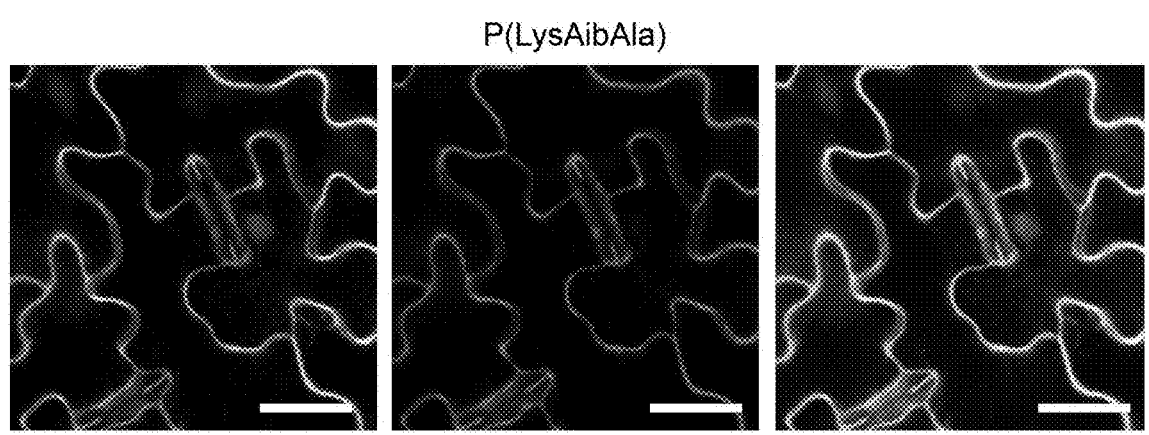

The results are shown in FIGS. 9A and 9B. As comparative examples, the results of Tat and R9 are also shown.

FIGS. 9A and 9B demonstrated that P (LysAibAla) represented by Formula (I) of the present invention can be more effectively introduced into plant cells compared with the known cell-penetrating sequence Tat, because the site exhibiting the TAMRA label-derived fluorescence is substantially consistent with the cytoplasm in which the yellow protein is present.

Example 2

<Synthesis of Cationic Carrier Peptide>

The following two types of cationic carrier peptides each bound to a maleimide group (MAL) via a spacer (tetraethylene glycol, TEG) as indicated below were synthesized by the Fmoc solid-phase synthesis method:

```
MAL-TEG-(KH)14 (partial sequence: KHKHKHKHKHKH
KHKHKHKHKHKHKHKH (SEQ ID NO: 3));
and MAL-TEG-(RH)14 (partial sequence: RHRHRHRHRHRH
RHRHRHRHRHRHRHRH (SEQ ID NO: 4)).
```

Peptide purity and molecular weight were confirmed using reverse phase high-performance liquid chromatography (RP-HPLC) and matrix-assisted laser desorption/ionization-time of flight (MALDI-TOF) mass spectrometry, respectively.

K represents lysine, H represents histidine, and R represents arginine.

<Synthesis of Polypeptide>

The tripeptide of the monomer LysAibAla; i.e. C-(LysAibAla)$_3$ in which cysteine (C) is bound to the N-terminus of lysine (sequence: CKXaaAKXaaAKXaaA, Xaa=Aib (SEQ ID NO: 5)), was synthesized by the Fmoc solid-phase synthesis method, and the purity and molecular weight thereof were confirmed using RP-HPLC and MALDI-TOF-MS, respectively.

<Preparation of Cationic Carrier Peptide-DNA Complex>

Plasmid DNA encoding Oplophorus gracilirostris-derived luciferase (NanoLuc) (pDNA, p35S-NanoLuc-tNos) was prepared. An aqueous solution of 2 mg/ml of MAL-TEG-(KH)$_{14}$ or MAL-TEG-(RH)$_{14}$ prepared above was mixed with an aqueous solution containing 20 μg of pDNA at the N/P ratio (i.e., the molar ratio of positively charged nitrogen contained in the cationic carrier peptide to negatively charged phosphorus contained in pDNA) of 2 to bring the total amount of the solution to 800 μl. The resulting mixtures were each incubated at 4° C. for 30 minutes to obtain the cationic carrier peptide-DNA complexes; i.e., MAL-TEG-(KH)-$_{14}$/pDNA and MAL-TEG-(RH)$_{14}$/pDNA.

<Modification of Cationic Carrier Peptide-DNA Complex with Polypeptide>

The maleimide group of each cationic carrier peptide and the thiol group of cysteine (C) of C-(LysAibAla)$_3$ were subjected to the addition reaction to obtain a complex modified with each of the polypeptides described above. Specific procedure will be described below.

To the solution (800 μl) containing each complex were added C-(LysAibAla)$_3$ prepared above and HEPES buffer (pH 7.6) so as to be the final concentration of 6 M and 5 mM, respectively, and the resultant was incubated at 25° C. for 1 hour with stirring to proceed the thiol/maleimide addition reaction.

After the reaction, the solution was analyzed by MALDI-TOF-MS to confirm the modification of the complex with C-(LysAibAla)$_3$. Also, the reaction solution was analyzed by RP-HPLC, and the unreacted C-(LysAibAla)$_3$ was quantified based on the peak area to calculate a modification rate of the maleimide group (5 μM) in the complex. In addition, the hydrodynamic diameter of the complex was determined by measuring dynamic light scattering (DLS).

MALDI-TOF-MS analysis was carried out using the ultrafleXtreme MALDI-TOF spectrometer (Bruker Daltonics) at the acceleration voltage of 15 kV in a reflective mode. The sample was dissolved in water/acetonitrile (0.8 mg/ml) containing 0.1% trifluoroacetic acid (TFA), and the resulting solution was mixed with a solution of α-cyano-4-hydroxycinnamic acid (CHCA) in water/acetonitrile (10 mg/ml) and then deposited on a target plate (MTP 384 ground steel BC target plate), followed by drying.

As a result of the analysis, peaks corresponding to the molecular weights of MAL-TEG-(KH)$_{14}$ and MAL-TEG-(RH)$_{14}$, each bound to C-(LysAibAla)$_3$, were observed. This clearly indicates that the complexes were modified with C-(LyAibAla)$_3$.

Specifically, Complexes 1 and 2 having the structures shown below were obtained.

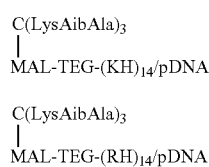

Complex 1

Complex 2

RP-HPLC analysis was performed using the HPLC system, which comprises the auto-sampler AS-2055, the gradient pump PU2089, the column oven CO-4060, the UV/vis detector UV-4075, and the gradient pump PU-2089 Plus (JASCO), and the YMC-Triart C18 column (particle size 5 μm, 150×4.6 mm, manufactured by YMC) at 25° C. and a flow rate of 1 ml/min. The mobile phase was composed of acetonitrile (Effluent A), Milli-Q water (Effluent B), and Milli-Q water supplemented with 0.1 v/v % TFA (Effluent C). Boc-Pro was used as the internal standard, and tris(2-carboxyethyl)phosphine (TCEP) was used as a reducing agent. The sample solution (100 μl) supplemented with Boc-Pro (final concentration, 100 μg/ml) and TCEP (final concentration, 50 mM) was injected, and the composition of the mobile phase was linearly changed from Effluents A:B:C=80%:10%:10% to Effluents A:B:C=35%:55%:10% over a period of 30 minutes for elution.

As a result of the quantification of unreacted C-(LysAibAla)$_3$ based on the peak area, the modification rates of the maleimide groups in Complex 1 and Complex 2 were estimated to be 88±7% and 78±5%, respectively.

The sample solution (800 μl) was transferred to the capillary cell (DTS1070, manufactured by Malalvern Panalytical), and DLS measurement was carried out using a zeta electrometer (manufactured by Zetasizer Nano-ZS, Malalvern Panalytical).

As a result of the measurement, the hydrodynamic diameters of Complex 1 and Complex 2 were 80±1 nm and 89±2 nm, respectively.

<Gene Transfer of Polypeptide-Modified Cationic Carrier Peptide-DNA Complex (Modified Complex) into Plant>

Nicotiana benthamiana was selected as a plant model, which was prepared by the procedures described below.

At the outset, seeds were germinated in pots with a culture medium that contained a 2:1 mixture of soil and vermiculite. The germinated plants were allowed to grow in a plant incubator (manufactured by Biotron NK system) at 22° C. under long-day conditions (the light period of 16 hours and the dark period of 8 hours) for 4 weeks. The leaves of the grown Nicotiana benthamiana were impregnated with an aqueous solution containing each of the modified complexes prepared above, and the plants were incubated in a plant incubator (Biotron NK system) for 16 hours. NanoLuc assay was then carried out in accordance with the protocols provided by the manufacturer (Promega Corporation), whereby the gene transfer efficiency was quantified. Specifically, a region of the leaf impregnated with the solution containing the complex was cut out into a disk shape with 1-cm diameter and then lysed in the Renilla Luciferase Assay Lysis Buffer (100 μl, manufactured by Promega Corporation). The lysate was centrifuged, and the obtained supernatant (50 μl) was added to a mixture (50 μl) of the Nano-Glo Luciferase Assay Substrate (Promega Corporation) and the Nano-Glo Lusiferase Assay Buffer (Promega Corporation) to measure the relative light unit (RLU) using a luminometer (GloMax20/20, Promega Corporation). The protein level in the supernatant was determined using the Bradford assay reagent (manufactured by Aproscience Inc.), and the relative light unit/weight of protein (RLU/mg protein) was determined. Also, the untreated leaves that were not impregnated with the solution of each modified complex were subjected to the same procedures to determine the RLU/mg protein, and the determined values were used as the background for correction. The mean±standard error (n=4) of the corrected RLU/mg protein was the gene transfer efficiency. As a negative control, leaves impregnated with an aqueous solution containing 20 μg of pDNA (p35S-Nano- Luc-tNOS) were subjected to the same experiment to calculate the gene transfer efficiency.

Figure 10:
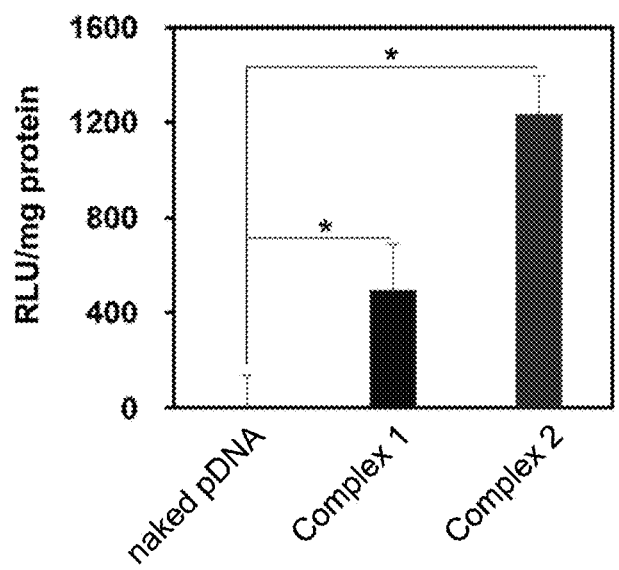
FIG. 10 shows gene transfer efficiency of nucleic acid-containing complexes 1 and 2, which have been modified with naked pDNA and (LysAibAla)$_3$ respectively, determined by NanoLuc assay using *Nicotiana benthamiana* leaves. The error bar represents the standard deviation (n=4), and the asterisk (*) represents the statistically significant difference (P<0.05, Mann-Whitney U-test).

FIG. 10 shows the gene transfer efficiency of Complex 1, Complex 2, and naked pDNA (negative control). The gene transfer efficiencies of Complex 1 and Complex 2 were significantly higher than that of the naked pDNA. The results demonstrate that the use of a nucleic acid-containing complex modified with C-(LysAibAla)$_3$ enables introduction of foreign genes into plants.

INDUSTRIAL APPLICABILITY

The present invention provides polypeptides that have substantially no cytotoxicity, high resistance to enzymatic degradation, and a high ability of cell invasion (i.e., internalization) over a long period of time. The polypeptides are capable of safely and efficiently transporting substances of interest into target cells, the polypeptides being thus applicable to fields including medicine, agriculture, and molecular biology.

SEQUENCE LISTING FREE TEXT

SEQ ID NOs: 1 to 5: Synthetic Peptides

The disclosures of all publications, patents, and patent applications cited herein are incorporated herein by reference in their entirety.

The invention claimed is:

1. A polypeptide having cell-penetrating ability and represented by Formula (I):

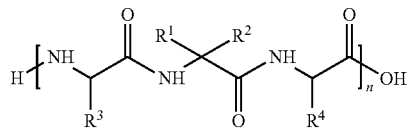

wherein n is 3; $R^1$ and $R^2$ represent a methyl group; $R^3$ represents a 4-aminobutyl group; $R^4$ represents a methyl group; and the N terminus and/or the C terminus of the polypeptide comprise a reactive functional group(s) capable of forming a complex between a cargo molecule and the polypeptide;

wherein the C terminus is modified by a $C_1$-$C_{10}$ alkoxy group or a $C_1$-$C_{10}$ monoalkylamino or dialkylamino group; and wherein the N terminus is modified by an acyl group, —C=O—R where R represents a $C_1$-$C_{10}$ alkyl group, an alkoxycarbonyl group, —C=O—OR where R represents a $C_1$-$C_{10}$ alkyl group, or a $C_1$-$C_{10}$ alkyl group in which one or more carbon atoms in the carbon chain may be substituted with an oxygen, nitrogen, or sulfur atom(s).

2. The polypeptide according to claim 1, wherein the reactive functional group is a maleimide-containing modification group or a thiol-containing modification group.

3. A kit for intracellular delivery comprising the polypeptide according to claim 1.

4. A cell-invasive composition comprising a polypeptide, as a first polypeptide, according to claim 1 and a substance of interest, wherein the substance of interest is united with the polypeptide or is present independently from the polypeptide.

5. The composition according to claim 4, wherein the substance of interest is selected from the group consisting of a protein, a peptide, a glycoprotein, a naturally-occurring or non-naturally-occurring nucleic acid, DNA, RNA, a DNA/RNA hybrid, an oligonucleotide, a polynucleotide, an antisense molecule, miRNA, siRNA, a plasmid, a low-molecular-weight compound, a sugar, a lipid, a glycolipid, a contrast substance, a drug, nanoparticles, and a quantum dot.

* * * * *